US011306347B2

(12) United States Patent
Dong et al.

(10) Patent No.: US 11,306,347 B2
(45) Date of Patent: Apr. 19, 2022

(54) IN VITRO AND CELL BASED ASSAYS FOR MEASURING THE ACTIVITY OF BOTULINUM NEUROTOXINS

(71) Applicant: President and Fellows of Harvard College, Cambridge, MA (US)

(72) Inventors: Min Dong, Weatogue, CT (US); Feifan Yu, Aberdeen, NJ (US)

(73) Assignee: President and Fellows of Harvard College, Cambridge, MA (US)

( * ) Notice: Subject to any disclaimer, the term of this patent is extended or adjusted under 35 U.S.C. 154(b) by 162 days.

(21) Appl. No.: 16/343,513

(22) PCT Filed: Oct. 19, 2017

(86) PCT No.: PCT/US2017/057411
§ 371 (c)(1),
(2) Date: Apr. 19, 2019

(87) PCT Pub. No.: WO2018/075783
PCT Pub. Date: Apr. 26, 2018

(65) Prior Publication Data
US 2019/0276873 A1    Sep. 12, 2019

Related U.S. Application Data

(60) Provisional application No. 62/410,558, filed on Oct. 20, 2016.

(51) Int. Cl.
| *C12Q 1/66* | (2006.01) |
| *C12N 9/02* | (2006.01) |
| *C12N 9/24* | (2006.01) |
| *C12N 9/52* | (2006.01) |
| *G01N 33/542* | (2006.01) |

(52) U.S. Cl.
CPC ............ *C12Q 1/66* (2013.01); *C12N 9/0069* (2013.01); *C12N 9/24* (2013.01); *C12N 9/52* (2013.01); *C12Y 304/24069* (2013.01); *G01N 33/542* (2013.01)

(58) Field of Classification Search
CPC .......... C12Q 1/66; C12N 9/0069; C12N 9/24; C12N 9/52; C12Y 304/24069; G01N 33/542
USPC ........................................................... 435/8
See application file for complete search history.

(56) References Cited

U.S. PATENT DOCUMENTS

| 4,518,584 | A | 5/1985 | Mark et al. |
| 4,737,462 | A | 4/1988 | Mark et al. |
| 4,950,588 | A | 8/1990 | Dattagupta |
| 5,004,565 | A | 4/1991 | Schaap |
| 5,098,828 | A | 3/1992 | Geiger et al. |
| 5,374,534 | A | 12/1994 | Zomer et al. |
| 5,455,357 | A | 10/1995 | Herrmann et al. |
| 6,436,682 | B1 | 8/2002 | Bryan et al. |
| 6,890,745 | B1 | 5/2005 | Leng |
| 8,557,970 | B2 | 10/2013 | Encell et al. |
| 2014/0235490 | A1 | 8/2014 | Kalkum et al. |

FOREIGN PATENT DOCUMENTS

| WO | WO-95/32738 A1 | 12/1995 |
| WO | WO-96/33273 A1 | 10/1996 |
| WO | WO-98/07864 A1 | 2/1998 |
| WO | WO-99/17806 A1 | 4/1999 |
| WO | WO-2005/038029 A2 | 4/2005 |
| WO | WO-2013/131991 A1 | 9/2013 |
| WO | WO-2018/075783 A2 | 4/2018 |

OTHER PUBLICATIONS

Bauer, C et al., A genetic enrichment for mutations constructed by oligodeoxynucleotide-directed mutagenesis, Gene, 37(1-3):73-81 (1985).
Binz, T., et al., Clostridial neurotoxins: mechanism of SNARE cleavage and outlook on potential substrate specificity reengineering, Toxins (Basel), 2(4):665-82 (2010).
Chen, X. et al., Fusion protein linkers: property, design and functionality, Adv Drug Deliv Rev., 65(10):1357-69 (2013).
Heise, K. et al., Dual luciferase assay for secreted luciferases based on Gaussia and NanoLuc, Assay Drug Dev Technol., 11(4):244-52 (2013).
Hill et al., Genetic diversity among Botulinum Neurotoxin-producing clostridial strains, J Bacteriol, 189(3): 818-832 (2007).
Humeau et al., How botulinum and tetanus neurotoxins block neurotransmitter release, Biochimie, 82(5):427-446 (2000).
International Search Report for PCT/US2017/057411 (In Vitro and Cell Based Assays for Measuring the Activity of Botulinum Neurotoxins, filed Oct. 19, 2017), issued by ISA/US, 8 pages (May 29, 2018).
Lalli et al., The Journey of tetanus and botulinum neurotoxins in neurons, Trends Microbiol, 11 (9): 431-437 (2003).
Leng, J. et al., CleavaliteTM: A Novel Bioluminescent Caspase Activity Assay, Abstracts of the Annual Meeting of the Society for Neurosci, 27(2): absract, 1 page (2001).

(Continued)

*Primary Examiner* — Jennifer M. H. Tichy
(74) *Attorney, Agent, or Firm* — Choate, Hall & Stewart LLP; Brenda Herschbach Jarrell; Stephanie L. Schonewald

(57) ABSTRACT

Disclosed herein are means for the detection and characterization of neurotoxins such as botulinum neurotoxin (BoNT) or tetanus neurotoxin. The present disclosure provides methods for determining potency and activity of neurotoxins in vitro and in vivo. Also disclosed are polypeptides comprising N- and C-terminal fragments of a reporter protein that are split by a linker comprising a neurotoxin cleavage site. Cleavage of the linker by a neurotoxin decreases reporter protein activity, thereby indicating activity of the neurotoxin. Compositions and kits comprising the disclosed polypeptides, nucleic acids comprising nucleotide sequences encoding such polypeptides, and cells expressing such polypeptides are also disclosed.

3 Claims, 4 Drawing Sheets

Specification includes a Sequence Listing.

(56) References Cited

OTHER PUBLICATIONS

Takenaka, Y. et al., Computational analysis and functional expression of ancestral copepod luciferase, Gene, 528(2):201-5 (2013).
Turton et al., Botulinum and Tetanus Neurotoxins: structure, function and therapeutic utility, Trends Biochem. Sci., 27(11): 552-558 (2002).
Turton, K. et al., Botulinum and tetanus neurotoxins: structure, function and therapeutic utility, TRENDS in Biochemical Sciences, 27(11):552-558 (2002).
Walder, R. and Walder, J., Oligodeoxynucleotide-directed mutagenesis using the yeast transformation system, Gene, 42(2):133-9 (1986).
Waud, J. et al., Engineering the C-terminus of firefly luciferase as an indicator of covalent modification of proteins, Biochimica et Biophysica Acta, 1292:89-98 (1996).
Written Opinion for PCT/US2017/057411 (In Vitro and Cell Based Assays for Measuring the Activity of Botulinum Neurotoxins, filed Oct. 19, 2017), issued by ISA/EP, 9 pages (May 29, 2018).
Zhao, H. et al., Characterization of coelenterazine analogs for measurements of Renilla luciferase activity in live cells and living animals, Mol Imaging, 3(1):43-54 (2004).

| | 4h | 24h |
|---|---|---|
| NNano-SV2C-p25-CNano | 9.73 pM | 7.86 pM |
| NNano-p25-CNano | 48.26 pM | 35.87 pM |

EC50 of cleavage N$_{Nano}$-VAMP1-C$_{Nano}$ by BoNT/B

- 4h
- 24h
- BoNT/A
- BoNT/B with Nano-SV2C-p25-CNano

FIG. 3A

|  | 4h | 24h |
|---|---|---|
| N Nano-VAMP1-C Nano | 75.7 pM | 3.9 pM |

SEQUENCE LISTING

<160> NUMBER OF SEQ ID NOS: 32

<210> SEQ ID NO 1
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Val Phe Thr Leu Glu Asp Phe Val Gly Asp Trp Glu Gln Thr Ala
1 5 10 15

Ala Tyr Asn Leu Asp Gln Val Leu Glu Gln Gly Gly Val Ser Ser Leu
20 25 30

Leu Gln Asn Leu Ala Val Ser Val Thr Pro Ile Gln Arg Ile Val Arg
35 40 45

Ser Gly Glu Asn Ala Leu Lys Ile Asp Ile His Val Ile Ile Pro Tyr
50 55 60

Glu Gly Leu Ser Ala Asp Gln Met Ala Gln Ile Glu Glu Val Phe Lys
65 70 75 80

```
Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser Val
145                 150                 155                 160

Thr Gly Tyr Arg Leu Phe Glu Glu Ile Leu
                165                 170

<210> SEQ ID NO 2
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser
145                 150                 155

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Val Thr Gly Tyr Arg Leu Phe Glu Glu Ile Leu
1               5                   10

<210> SEQ ID NO 4
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ser Ser Gly Gly Gly Gly Ser Gly Gly Gly Ser Ser Gly
1               5                   10                  15

<210> SEQ ID NO 5
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ser Ser Gly Gly Gly Gly Ser Gly Gly Gly Ser Ser Gly
1               5                   10

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Ser
1               5

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(15)
<223> OTHER INFORMATION: /note="This sequence may encompass 1-3 'Gly Gly
      Gly Gly Ser' repeating units"

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Lys Glu Ser Gly Ser Val Ser Ser Glu Gln Leu Ala Gln Phe Arg Ser
1               5                   10                  15

Leu Asp
```

```
<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Glu Gly Lys Ser Ser Gly Ser Gly Ser Glu Ser Lys Ser Thr
1               5                   10

<210> SEQ ID NO 10
<211> LENGTH: 66
<212> TYPE: PRT
<213> ORGANISM: Unknown
<220> FEATURE:
<221> NAME/KEY: source
<223> OTHER INFORMATION: /note="Description of Unknown: Human or rat
      SNAP25b polypeptide"

<400> SEQUENCE: 10

Ala Arg Glu Asn Glu Met Asp Glu Asn Leu Glu Gln Val Ser Gly Ile
1               5                   10                  15

Ile Gly Asn Leu Arg His Met Ala Leu Asp Met Gly Asn Glu Ile Asp
                20                  25                  30

Thr Gln Asn Arg Gln Ile Asp Arg Ile Met Glu Lys Ala Asp Ser Asn
            35                  40                  45

Lys Thr Arg Ile Asp Glu Ala Asn Gln Arg Ala Thr Lys Met Leu Gly
        50                  55                  60

Ser Gly
65

<210> SEQ ID NO 11
<211> LENGTH: 38
<212> TYPE: PRT
<213> ORGANISM: Homo sapiens

<400> SEQUENCE: 11

Asn Thr Tyr Phe Lys Asn Cys Thr Phe Ile Asp Thr Val Phe Asp Asn
1               5                   10                  15

Thr Asp Phe Glu Pro Tyr Lys Phe Ile Asp Ser Glu Phe Lys Asn Cys
                20                  25                  30

Ser Phe Phe His Asn Lys
            35

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 12

His His His His His His
1               5

<210> SEQ ID NO 13
<211> LENGTH: 550
<212> TYPE: PRT
<213> ORGANISM: Photinus pyralis
```

<400> SEQUENCE: 13

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
                20                  25                  30
Tyr Ala Leu Val Pro Gly Thr Ile Ala Phe Thr Asp Ala His Ile Glu
            35                  40                  45
Val Asp Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Gly Ile Ser Gln Pro Thr Val Val Phe Val
        115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
```

```
Trp Leu His Ser Gly Asp Ile Ala Tyr Trp Asp Asp Glu His Phe
            420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
                530                 535                 540

Gly Gly Lys Ile Ala Val
545                 550

<210> SEQ ID NO 14
<211> LENGTH: 206
<212> TYPE: PRT
<213> ORGANISM: Homo sapiens

<400> SEQUENCE: 14

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 15
<211> LENGTH: 981
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
atggtcttca cactcgaaga tttcgttggg gactgggaac agacagccgc ctacaacctg      60
gaccaagtcc ttgaacaggg aggtgtgtcc agtttgctgc agaatctcgc cgtgtccgta     120
actccgatcc aaaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgacggctcc atgctgttcc gagtaaccat caacagtggg     480
agttccggtg gtggcgggag cggaggtgga ggctcgagcg tggagctcga aacacctac      540
ttcaagaact gcacatttat tgacactgtt tttgacaaca cagattttga gccatataaa     600
ttcattgaca gtgaatttaa aaactgctcg ttttttcaca acaagggggg cggaggttcc     660
gcccgggaaa atgaaatgga tgaaaaccta gagcaggtga gcggcatcat cggaaacctc     720
cgtcatatgg ccctagacat gggcaatgag attgacaccc agaatcgcca gattgacagg     780
atcatggaga aggctgactc caacaaaacc agaattgatg aagccaacca acgtgcaaca     840
aagatgctgg gaagtggtgg gaattctggc tcgagcggtg gtggcgggag cggaggtgga     900
gggtcgtcag gtgtgaccgg ctaccggctg ttcgaggaga ttctggcggc cgcactcgag     960
caccaccacc accaccactg a                                               981
```

<210> SEQ ID NO 16
<211> LENGTH: 118
<212> TYPE: PRT
<213> ORGANISM: Homo sapiens

<400> SEQUENCE: 16

Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
        115

<210> SEQ ID NO 17
<211> LENGTH: 21
<212> TYPE: PRT
<213> ORGANISM: Homo sapiens

<400> SEQUENCE: 17

Gly Glu Gly Lys Glu Asp Ala Phe Ser Lys Leu Lys Gln Lys Phe Met
1               5                   10                  15

Asn Glu Leu His Lys
            20

<210> SEQ ID NO 18
<211> LENGTH: 21
<212> TYPE: PRT
<213> ORGANISM: Homo sapiens

<400> SEQUENCE: 18

Gly Glu Ser Gln Glu Asp Met Phe Ala Lys Leu Lys Glu Lys Phe Phe
1               5                   10                  15

Asn Glu Ile Asn Lys
            20

<210> SEQ ID NO 19
<211> LENGTH: 28
<212> TYPE: PRT
<213> ORGANISM: Homo sapiens

<400> SEQUENCE: 19

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys
            20                  25

<210> SEQ ID NO 20
<211> LENGTH: 28
<212> TYPE: PRT
<213> ORGANISM: Homo sapiens

<400> SEQUENCE: 20

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys
            20                  25

<210> SEQ ID NO 21
<211> LENGTH: 28
<212> TYPE: PRT
<213> ORGANISM: Homo sapiens

<400> SEQUENCE: 21

Leu Ser Glu Leu Asp Asp Arg Ala Asp Ala Leu Gln Ala Gly Ala Ser
1               5                   10                  15

Gln Phe Glu Ser Ser Ala Ala Lys Leu Lys Arg Lys
            20                  25

<210> SEQ ID NO 22

<400> SEQUENCE: 22

000

<210> SEQ ID NO 23
<211> LENGTH: 206
<212> TYPE: PRT
<213> ORGANISM: Homo sapiens

<400> SEQUENCE: 23

```
Met Ala Glu Asp Ala Asp Met Arg Asn Glu Leu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
            85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
            165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 24
<211> LENGTH: 118
<212> TYPE: PRT
<213> ORGANISM: Homo sapiens

<400> SEQUENCE: 24

Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
            85                  90                  95

Met Met Ile Met Leu Gly Ala Ile Cys Ala Ile Ile Val Val Val Ile
            100                 105                 110

Val Ile Tyr Phe Phe Thr
        115

<210> SEQ ID NO 25
<211> LENGTH: 116
<212> TYPE: PRT
<213> ORGANISM: Homo sapiens

<400> SEQUENCE: 25
```

```
Met Ser Ala Thr Ala Thr Ala Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Val
            100                 105                 110

Tyr Phe Ser Thr
            115

<210> SEQ ID NO 26
<211> LENGTH: 100
<212> TYPE: PRT
<213> ORGANISM: Homo sapiens

<400> SEQUENCE: 26

Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
            20                  25                  30

Val Asp Lys Val Leu Glu Arg Asp Gln Lys Leu Ser Glu Leu Asp Asp
        35                  40                  45

Arg Ala Asp Ala Leu Gln Ala Gly Ala Ser Gln Phe Glu Thr Ser Ala
    50                  55                  60

Ala Lys Leu Lys Arg Lys Tyr Trp Trp Lys Asn Cys Lys Met Trp Ala
65                  70                  75                  80

Ile Gly Ile Thr Val Leu Val Ile Phe Ile Ile Ile Ile Val Trp
                85                  90                  95

Val Val Ser Ser
            100

<210> SEQ ID NO 27
<211> LENGTH: 288
<212> TYPE: PRT
<213> ORGANISM: Homo sapiens

<400> SEQUENCE: 27

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95
```

```
Glu Gln Ser Ile Glu Gln Glu Gly Leu Asn Arg Ser Ser Ala Asp
                100                 105                 110

Leu Arg Ile Arg Lys Thr Gln His Ser Thr Leu Ser Arg Lys Phe Val
            115                 120                 125

Glu Val Met Ser Glu Tyr Asn Ala Thr Gln Ser Asp Tyr Arg Glu Arg
        130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
1   210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285

<210> SEQ ID NO 28
<211> LENGTH: 288
<212> TYPE: PRT
<213> ORGANISM: Homo sapiens

<400> SEQUENCE: 28

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
                20                  25                  30

Phe Glu Gln Val Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
                100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
```

180                 185                 190
Glu Ile Glu Thr Arg His Asn Glu Ile Ile Lys Leu Glu Thr Ser Ile
                195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 29
<211> LENGTH: 852
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
atggtcttca cactcgaaga tttcgttggg gactgggaac agacagccgc ctacaacctg     60
gaccaagtcc ttgaacaggg aggtgtgtcc agtttgctgc agaatctcgc cgtgtccgta    120
actccgatcc aaaggattgt ccggagcggt gaaaatgccc tgaagatcga catccatgtc    180
atcatcccgt atgaaggtct gagcgccgac caaatggccc agatcgaaga ggtgtttaag    240
gtggtgtacc ctgtggatga tcatcacttt aaggtgatcc tgccctatgg cacactggta    300
atcgacgggg ttacgccgaa catgctgaac tatttcggac ggccgtatga aggcatcgcc    360
gtgttcgacg gcaaaaagat cactgtaaca gggaccctgt ggaacggcaa caaaattatc    420
gacgagcgcc tgatcacccc cgacggctcc atgctgttcc gagtaaccat caacagtggg    480
agttccggtg gtggcgggag cggaggtgga ggctcgagcg gtggagctca ggcccgggaa    540
aatgaaatgg atgaaaacct agagcaggtg agcggcatca tcggaaacct ccgtcatatg    600
gccctagaca tgggcaatga gattgacacc cagaatcgcc agattgacag gatcatggag    660
aaggctgact ccaacaaaac cagaattgat gaagccaacc aacgtgcaac aaagatgctg    720
ggaagtggtg ggaattctgg ctcgagcggt ggtggcggga gcggaggtgg agggtcgtca    780
ggtgtgaccg gctaccggct gttcgaggag attctggcgg ccgcactcga gcaccaccac    840
caccaccact ga                                                        852

<210> SEQ ID NO 30
<211> LENGTH: 840
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
atggtcttca cactcgaaga tttcgttggg gactgggaac agacagccgc ctacaacctg     60
gaccaagtcc ttgaacaggg aggtgtgtcc agtttgctgc agaatctcgc cgtgtccgta    120
actccgatcc aaaggattgt ccggagcggt gaaaatgccc tgaagatcga catccatgtc    180

```
atcatcccgt atgaaggtct gagcgccgac caaatggccc agatcgaaga ggtgtttaag      240
gtggtgtacc ctgtggatga tcatcacttt aaggtgatcc tgccctatgg cacactggta      300
atcgacgggg ttacgccgaa catgctgaac tatttcggac ggccgtatga aggcatcgcc      360
gtgttcgacg gcaaaaagat cactgtaaca gggaccctgt ggaacggcaa caaaattatc      420
gacgagcgcc tgatcacccc cgacggctcc atgctgttcc gagtaaccat caacagtggg      480
agttccggtg gtggcgggag cggaggtgga ggctcgagcg gtggagctca gcagcaaacc      540
caggcacaag tggaggaggt ggtggacatc atacgtgtga acgtggacaa ggtcctggag      600
agggaccaga agctgtcaga gctggatgac cgagctgatg ccttgcaggc aggagcatca      660
caatttgaga gcagtgctgc caagctaaag aggaagtatt ggtggaaaaa ctgcaagggg      720
aattctggct cgagcggtgg tggcgggagc ggaggtggag ggtcgtcagg tgtgaccggc      780
taccggctgt tcgaggagat tctggcggcc gcactcgagc accaccacca ccaccactga      840
```

<210> SEQ ID NO 31
<211> LENGTH: 2898
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

```
atggtcttca cactcgaaga tttcgttggg gactgggaac agacagccgc ctacaacctg       60
gaccaagtcc ttgaacaggg aggtgtgtcc agtttgctgc agaatctcgc cgtgtccgta      120
actccgatcc aaaggattgt ccggagcggt gaaaatgccc tgaagatcga catccatgtc      180
atcatcccgt atgaaggtct gagcgccgac caaatggccc agatcgaaga ggtgtttaag      240
gtggtgtacc ctgtggatga tcatcacttt aaggtgatcc tgccctatgg cacactggta      300
atcgacgggg ttacgccgaa catgctgaac tatttcggac ggccgtatga aggcatcgcc      360
gtgttcgacg gcaaaaagat cactgtaaca gggaccctgt ggaacggcaa caaaattatc      420
gacgagcgcc tgatcacccc cgacggctcc atgctgttcc gagtaaccat caacagtggg      480
agttccggtg gtggcgggag cggaggtgga ggctcgagcg gtggagctca ggaagatgcc      540
aaaaacatta gaagggccca gcgccattc tacccactcg aagacgggac cgccggcgag      600
cagctgcaca agccatgaa gcgctacgcc ctggtgcccg gcaccatcgc ctttaccgac      660
gcacatatcg aggtggacat tacctacgcc gagtacttcg agatgagcgt tcggctggca      720
gaagctatga agcgctatgg gctgaataca aaccatcgga tcgtggtgtg cagcgagaat      780
agcttgcagt tcttcatgcc cgtgttgggt gccctgttca tcggtgtggc tgtggcccca      840
gctaacgaca tctacaacga gcgcgagctg ctgaacagca tgggcatcag ccagcccacc      900
gtcgtattcg tgagcaagaa agggctgcaa aagatcctca acgtgcaaaa gaagctaccg      960
atcatacaaa agatcatcat catggatagc aagaccgact accagggctt ccaaagcatg     1020
tacaccttcg tgacttccca tttgccaccc ggcttcaacg agtacgactt cgtgcccgag     1080
agcttcgacc gggacaaaac catcgccctg atcatgaaca gtagtggcag taccggattg     1140
cccaagggcg tagccctacc gcaccgcacc gcttgtgtcc gattcagtca tgcccgcgac     1200
cccatcttcg gcaaccagat catccccgac accgctatcc tcagcgtggt gccatttcac     1260
cacggcttcg gcatgttcac cacgctgggc tacttgatct gcggctttcg ggtcgtgctc     1320
```

```
atgtaccgct tcgaggagga gctattcttg cgcagcttgc aagactataa gattcaatct    1380
gccctgctgg tgcccacact atttagcttc ttcgctaaga gcactctcat cgacaagtac    1440
gacctaagca acttgcacga gatcgccagc ggcggggcgc cgctcagcaa ggaggtaggt    1500
gaggccgtgg ccaaacgctt ccacctacca ggcatccgcc agggctacgg cctgacagaa    1560
acaaccagcg ccattctgat caccccgaa ggggacgaca gcctggcgc agtaggcaag      1620 gtggtgccct tcttcgaggc taaggtggtg gacttggaca ccggtaagac actgggtgtg    1680
aaccagcgcg cgagctgtg cgtccgtggc cccatgatca tgagcggcta cgttaacaac     1740
cccgaggcta caaacgctct catcgacaag gacggctggc tgcacagcgg cgacatcgcc    1800
tactgggacg aggacgagca cttcttcatc gtggaccggc tgaagagcct gatcaaatac    1860
aagggctacc aggtagcccc agccgaactg gagagcatcc tgctgcaaca ccccaacatc    1920
ttcgacgccg ggtcgccgg cctgccgac gacgatgccg gcgagctgcc cgccgcagtc      1980
gtcgtgctgg aacacggtaa aaccatgacc gagaaggaga tcgtggacta tgtggccagc    2040
caggttacaa ccgccaagaa gctgcgcggt ggtgttgtgt cgtggacga ggtgcctaaa     2100 ggactgaccg gcaagttgga cgcccgcaag atccgcgaga ttctcattaa ggccaagaag    2160
ggcggcaaga tcgccgtggg gggcggaggt tccgccgagg acgcagacat gcgtaatgaa    2220
ctggaggaga tgcagaggag ggctgaccag ctggctgatg agtccctgga agcacccgt     2280 cgcatgctgc agctggtcga agagagtaaa gatgctggca tcaggacttt ggttatgttg    2340
gatgagcaag gcgaacaact ggaacgcatt gaggaaggga tggaccaaat caataaggat    2400
atgaaagaag cagaaaagaa tttgacggac ctaggaaaat tctgcgggct ttgtgtgtgt    2460
ccctgtaaca agcttaaatc cagtgatgct tacaaaaaag cctggggcaa taatcaggat    2520
ggagtagtgg ccagccagcc tgcccgtgtg gtggatgaac gggagcagat ggccatcagt    2580
ggtggcttca tccgcagggt aacaaacgat gcccgggaaa atgaaatgga tgaaaaccta    2640
gagcaggtga gcggcatcat cggaaacctc cgtcatatgg ccctagacat gggcaatgag    2700
attgacaccc agaatcgcca gattgacagg atcatggaga aggctgactc caacaaaacc    2760
agaattgatg aagccaacca acgtgcaaca aagatgctgg gaagtggtgg gaattctggc    2820
tcgagcggtg gtggcgggag cggaggtgga gggtcgtcag gtgtgaccgg ctaccggctg    2880
ttcgaggaga ttctgtaa                                                  2898
```

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ser Ser Gly Gly Gly Gly Ser Gly Gly Gly Ser Ser Gly Gly
1               5                   10                  15

IN VITRO AND CELL BASED ASSAYS FOR MEASURING THE ACTIVITY OF BOTULINUM NEUROTOXINS

CROSS REFERENCE TO RELATED APPLICATIONS

The present application claims the benefit of U.S. Provisional Application No. 62/410,558, filed Oct. 20, 2016, the content of which is hereby incorporated by reference herein in its entirety.

SEQUENCE LISTING

The present specification makes reference to a Sequence Listing (submitted electronically as a .txt file named "0342941_0630_SL.TXT"). The .txt file was generated on Oct. 13, 2017, and is 34,305 bytes in size. The entire contents of the Sequence Listing are herein incorporated by reference.

TECHNICAL FIELD

The technology described herein relates to methods and compositions for determining the activity of neurotoxins, e.g., botulinum toxin.

BACKGROUND

Botulinum neurotoxin (BoNT) is an agent of interest both for bioterrorism concerns as well as therapeutic applications. Traditionally, detection and characterization of BoNT has been performed by administering samples to mice, causing their death at significant doses. Assays which can be performed with cells or in vitro have been explored, but suffer from a lack of sensitivity or specificity, often causing positive signals as a result of reactions with common components of clinical samples.

SUMMARY

Described herein are new assays developed to detect and measure the activity of BoNTs both in vitro and in vivo. The assays use unique single chain polypeptides that feature, e.g., a split luciferase linked through substrates of BoNTs engineered to serve as a sensor for BoNT activity. In the presence of BoNT, the linker region is cleaved by the toxin resulting in a decrease in luciferase activity, which is readily detected.

In one aspect of any of the embodiments, described herein is a single chain polypeptide comprising, from N-terminal to C-terminal: a) an N-terminal fragment of a reporter protein; b) a linker comprising a neurotoxin cleavage site; and c) a C-terminal fragment of the reporter protein; wherein the N-terminal and C-terminal fragments collectively comprise a functional reporter protein sequence; and wherein the linker functionally joins the N-terminal fragment and C-terminal fragment to generate a functional reporter fusion protein. In some embodiments of any of the aspects, the reporter protein is a luciferase protein.

In one aspect of any of the embodiments, described herein is a single chain polypeptide comprising: a) a N-terminal domain comprising a sequence with at least 90% sequence identity to amino acids 1-159 of the luciferase of SEQ ID NO: 1 (N-nano$_{1-159}$); b) a linker comprising a neurotoxin cleavage site located C-terminal to the N-nano$_{1-159}$; and c) a C-terminal domain having a sequence with at least 90% sequence identity amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In one aspect of any of the embodiments, described herein is a single chain polypeptide comprising: a) a N-terminal domain comprising a sequence having less than 10 amino acid residues substitutions, deletions, or additions relative to amino acids 1-159 of the luciferase of SEQ ID NO: 1 (N-nano$_{1-159}$); b) a linker comprising a neurotoxin cleavage site located C-terminal to the N-nano$_{1-159}$; and c) a C-terminal domain having a sequence having less than 3 amino acid residues substitutions, deletions, or additions relative to amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In some embodiments of any of the aspects, the N-terminal domain has the sequence of amino acids 1-159 of the luciferase of SEQ ID NO: 1 (N-nano$_{1-159}$) and the C-terminal domain has the sequence of amino acids 160-170 of the luciferase of SEQ ID NO: 1 (C-nano$_{160-170}$). In some embodiments of any of the aspects, the neurotoxin cleavage site is a C. botulinum neurotoxin (BoNT) and/or a Tetanus neurotoxin cleavage site.

In some embodiments of any of the aspects, the linker further comprises one or more spacers located between the BoNT cleavage site and the N-terminal fragment or domain, between the neurotoxin cleavage site and the C-terminal fragment of domain, or a combination thereof. In some embodiments of any of the aspects, the linker further comprises a binding fragment of a receptor for the BoNT and/or a tetanus neurotoxin. In some embodiments of any of the aspects, the binding fragment is located between the N-terminal fragment or domain and the BoNT cleavage site. In some embodiments of any of the aspects, the linker further comprises a spacer located between the binding fragment and the BoNT cleavage site. In some embodiments of any of the aspects, at least one spacer is comprised of glycine and serine. In some embodiments of any of the aspects, at least one spacer is 5 to 15 amino acids. In some embodiments of any of the aspects, at least one spacer is selected from SEQ ID NOs: 4-9.

In some embodiments of any of the aspects, the BoNT is A, E, C, B, D, F or G. In some embodiments of any of the aspects, the BoNT cleavage site is from a SNARE protein. In some embodiments of any of the aspects, the SNARE protein is SNAP-25, synaptobrevin (VAMP), or syntaxin. In some embodiments of any of the aspects, the BoNT cleavage site is amino acids 141-206 of human SNAP-25b. In some embodiments of any of the aspects, the BoNT cleavage site is amino acid 35-96 of human VAMP'. In some embodiments of any of the aspects, the receptor is human SV2C. In some embodiments of any of the aspects, the binding fragment is amino acids 529-566 of human SV2C, or a sequence having at least 90% identity with amino acids 529-566 of human SV2C, or a sequence with no more than 10 amino acid residues substitutions, deletions, or additions relative to amino acids 529-566 of human SV2C.

In some embodiments of any of the aspects, the polypeptide further comprises a polyhistidine affinity tag. In some embodiments of any of the aspects, the polyhistidine affinity tag is located at the C-terminus of the polypeptide.

In some embodiments of any of the aspects, the linker further comprises an intact second luciferase polypeptide located between the N-terminal fragment or domain and the BoNT cleavage site. In some embodiments of any of the aspects, the second luciferase polypeptide is firefly luciferase (e.g., *Photinus pyrahs*), bacterial luciferase (e.g., *Vibrio fischeri, Vibrio harveyi*), sea pansy luciferase (*Renilla reniformis*), dinoflagellate luciferase, *Gaussia* luciferase, or copepod luciferase. In some embodiments of any of the aspects, the linker further comprises a spacer located between the second luciferase polypeptide and the BoNT cleavage site. In some embodiments of any of the aspects, the spacer is from 5 to 15 amino acids. In some embodiments of any of the aspects, the spacer is GSSGGGGSGGGGSSG (SEQ ID NO: 4), GSSGGGGSGGGSSG (SEQ ID NO: 5), or GGGGS (SEQ ID NO: 6).

In one aspect of any of the embodiments, described herein is a single chain polypeptide comprising: a) amino acids 1-159 of the luciferase of SEQ ID NO: 1 (N-nano$_{1-159}$); b) a linker located C-terminal to the N-nano$_{1-159}$ comprising: i) a first spacer of 5 to 15 amino acids; ii) a binding fragment comprised of amino acids 529-566 of SV2C located C-terminal to the first spacer; iii) a second spacer located C-terminal to the binding fragment; iv) a BoNT cleavage site comprising amino acids 141-206 of human SNAP25b located C-terminal to the second spacer; v) a third spacer of 5 to 15 amino acids located C-terminal to the BoNT cleavage site; and c) amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In one aspect of any of the embodiments, described herein is a single chain polypeptide comprising: a) amino acids 1-159 of the luciferase of SEQ ID NO: 1 (N-nano$_{1-159}$); b) a linker located C-terminal to the N-nano$_{1-159}$ comprising: i) a first spacer from 5 to 15 amino acids; ii) a BoNT cleavage site comprising amino acids 141-206 of human SNAP25b located C-terminal to the first spacer; iii) a second spacer of 5 to 15 amino acids located C-terminal to the BoNT cleavage site; and c) amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In one aspect of any of the embodiments, described herein is a single chain polypeptide comprising: a) amino acids 1-159 of the luciferase of SEQ ID NO: 1 (N-nano$_{1-159}$); b) a linker located C-terminal to the N-nano$_{1-159}$ comprising: i) a first spacer of 5 to 15 amino acids; ii) a BoNT cleavage site comprising amino acids 35-96 of human VAMP1 located C-terminal to the first spacer; iii) a second spacer of 5 to 15 amino acids located C-terminal to the BoNT cleavage site; and c) amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In one aspect of any of the embodiments, described herein is a single chain polypeptide comprising: a) amino acids 1-159 of the luciferase of SEQ ID NO: 1 (N-nano$_{1-159}$); b) a linker located C-terminal to the N-nano$_{1-159}$ comprising: i) a second functional luciferase polypeptide; ii) a first spacer of 5 to 15 amino acids located C-terminal of the second luciferase polypeptide; iii) a BoNT cleavage site comprising amino acids 1-206 of human SNAP25b located C-terminal to the first spacer; iv) a second spacer of 5 to 15 amino acids located C-terminal to the BoNT cleavage site; and c) amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In some embodiments of any of the aspects, one or more spacers are GSSGGGGSGGGGSSG (SEQ ID NO: 4), GSSGGGGSGGGSSG (SEQ ID NO: 5), or GGGGS (SEQ ID NO: 6). In some embodiments of any of the aspects, the polypeptide further comprises a His6 sequence (SEQ ID NO: 12) located at the C-terminus.

In one aspect of any of the embodiments, described herein is a nucleic acid comprising a nucleotide sequence that encodes a single chain polypeptide described herein. In one aspect of any of the embodiments, described herein is a nucleic acid vector comprising a nucleic acid comprising a nucleotide sequence that encodes a single chain polypeptide described herein. In some embodiments of any of the aspects, the vector is an expression vector and comprises the nucleic acid sequence in expressible form. In some embodiments of any of the aspects, the vector is selected from the group consisting of a viral expression vector, a prokaryotic expression vector, a yeast expression vector, an insect expression vector, or a mammalian expression vector.

In one aspect of any of the embodiments, described herein is a cell comprising a nucleic acid or vector of the foregoing paragraph. In some embodiments of any of the aspects, the cell expresses a single chain polypeptide as described herein. In some embodiments of any of the aspects, the cell is a prokaryotic cell, a yeast cell, an insect cell, or an animal cell.

In one aspect of any of the embodiments, described herein is a method for determining the potency of a botulinum neurotoxin, comprising: contacting the neurotoxin to a single chain polypeptide as described herein under conditions appropriate for BoNT activity; and determining the luciferase activity of the polypeptide, as compared to a reference, thereby determining the potency.

In one aspect of any of the embodiments, described herein is a method for detecting *C. botulinum* neurotoxin (BoNT) activity in a sample, comprising: contacting the sample to a single chain polypeptide as described herein under conditions appropriate for BoNT activity; and determining luciferase activity of the polypeptide, as compared to luciferase activity of the polypeptide in the absence of the sample, wherein a decrease of luciferase activity indicates BoNT activity in the sample.

In some embodiments of any of the aspects, the method is performed in vitro. In some embodiments of any of the aspects, contacting occurs in a buffer of 50 mM HEPES, 20 μM ZnCl$_2$, 2 mM DTT, 1 mg/ml BSA, pH 7.1. In some embodiments of any of the aspects, the concentration of the single chain polypeptide contacted to the sample is from about 30 nM to 300 nM. In some embodiments of any of the aspects, the concentration of single chain polypeptide contacted to the sample is about 30 nM.

In some embodiments of any of the aspects, the luciferase activity is determined by addition of luciferase substrate to the single chain polypeptide and quantitative measurement of a luminescent signal produced. In some embodiments of any of the aspects, the conditions comprise incubation at about 37° C. for a period of from about 1 hour to about 36 hours. In some embodiments of any of the aspects, the conditions comprise incubation at about 37° C. for a period of from about 1 hour to about 24 hours. In some embodiments of any of the aspects, the conditions comprise incubation at about 37° C. for a period of from about 4 hours to about 24 hours.

In some embodiments of any of the aspects, the linker comprises a first spacer of 5 to 15 amino acids, a binding fragment of amino acids 529-566 of human SV2C located C-terminal to the first spacer and N-terminal to the BoNT cleavage site, and a second spacer of 5 to 15 amino acids located C-terminal to the BoNT cleavage site, wherein the BoNT cleavage site comprises amino acids 141-206 of human SNAP25. In some embodiments of any of the aspects, the linker comprises a first spacer of 5 to 15 amino acids located N-terminal to the BoNT cleavage site, and a second spacer of 5 to 15 amino acids located C-terminal to the BoNT cleavage site, wherein the BoNT cleavage site comprises amino acids 141-206 of human SNAP25. In some embodiments of any of the aspects, the linker comprises a first spacer of 5 to 15 amino acids located N-terminal to the BoNT cleavage site, a second spacer of 5 to 15 amino acids located C-terminal to the BoNT cleavage site, wherein the BoNT cleavage site comprises amino acids 35-96 of human VAMP1.

In some embodiments of any of the aspects, the single chain polypeptide is expressed by a neuronal cell and the method further comprises, after the contacting step: incubating the neuronal cells for a period of from about 12 hours to about 60 hours and harvesting lysate from the neuronal cells.

In one aspect of any of the embodiments, described herein is a method for detecting C. botulinum neurotoxin (BoNT) activity in a sample, comprising: a) contacting the sample to neuronal cells expressing a single chain polypeptide comprising: amino acids 1-159 of the luciferase of SEQ ID NO: 1 (N-nano$_{1-159}$), amino acids 160-170 of the luciferase of SEQ ID NO: 1 (C-nano$_{160-170}$), separated and functionally joined by a linker comprising a BoNT cleavage site located C-terminal to the N-nano$_{1-159}$ and N-terminal to the C-nano$_{160-170}$ b) incubating the neuronal cells for a period of from about 12 hours to about 60 hours; c) harvesting lysate from the neuronal cells; and d) measuring luciferase activity in the lysate, as compared to luciferase activity in identically treated neuronal cells in the absence of the sample, wherein a decrease in the luciferase activity indicates BoNT activity in the sample.

In some embodiments of any of the aspects, the linker further comprises an intact second luciferase polypeptide located between the N-nano$_{1-159}$ and the cleavage site. In some embodiments of any of the aspects, the second luciferase polypeptide firefly luciferase (Photinus pyralis), bacterial luciferase (Vibrio fischiri, Vibrio harveyi), sea pansy luciferase (Renilla reniformis), dinoflagellate luciferase, gaussia luciferase, or copepod luciferase. In some embodiments of any of the aspects, the luciferase activity of the second luciferase polypeptide in the sample is determined and used as an indicator of total single chain polypeptide present in the harvested lysate. In some embodiments of any of the aspects, the neuronal cells express the single chain polypeptide from a viral expression vector. In some embodiments of any of the aspects, the single chain polypeptide is expressed for 6 days prior to step a). In some embodiments of any of the aspects, the viral expression system is a lentivirus expression system.

In some embodiments of any of the aspects, the incubating step is about 48 hours. In some embodiments of any of the aspects, the harvesting step is by addition of a lysis buffer.

In some embodiments of any of the aspects, the BoNT cleavage site is from SNAP-25, synaptobrevin (VAMP), or syntaxin. In some embodiments of any of the aspects, the BoNT cleavage site is specifically recognized by BoNT A, E and C, or is specifically recognized by BoNT B, D, F and G. In some embodiments of any of the aspects, a combination of single chain polypeptides having different BoNT cleavage sites are used. In some embodiments of any of the aspects, the BoNT cleavage site is a.a.141-206 of human SNAP-25, or a.a. 35-96 of human VAMP1, a.a. 1-206 of human SNAP35, or a.a. 1-96 of VAMP1. In some embodiments of any of the aspects, the linker further comprises a binding fragment of a BoNT receptor. In some embodiments of any of the aspects, the receptor is SV2C. In some embodiments of any of the aspects, the binding fragment comprises amino acids 529-566 of human SV2C.

In some embodiments of any of the aspects, the linker comprises a second luciferase polypeptide, a first spacer of 5 to 15 amino acids located C-terminal of the second luciferase polypeptide and N-terminal of the BoNT cleavage site, a second spacer of 5 to 15 amino acids located C-terminal to the BoNT cleavage site, wherein the BoNT cleavage site comprises amino acid 1-206 of human SNAP25 and is located C-terminal to the first spacer.

In some embodiments of any of the aspects, the measurement of luciferase activity is accomplished by addition of a substrate specific for the luciferase and quantitative detection of the resulting luminescent signal. In some embodiments of any of the aspects, the substrate for the luciferase of SEQ ID NO: 1 is furimazine (2-furanylmethyl-deoxy-coelenterazine).

In one aspect, described herein is a kit comprising: a) one or more single chain polypeptides as described herein, with each or a combination of the single chain polypeptides packaged into a separate container; b) one or more nucleic acids or nucleic acid vectors as described herein, with each or a combination of the nucleic acids or nucleic acid vectors packaged into a separate container; and/or c) one or more cells as described herein with each or a combination of the cells packaged into a separate container. In some embodiments of any of the aspects, the kit further comprises a luciferase substrate packaged into a separate container.

BRIEF DESCRIPTION OF THE DRAWINGS

FIG. 3A-FIG. 3B demonstrate an in vitro detection assay of BoNT/B after 4 h and 24 h. The sensor protein $N_{Nano}$-VAMP1-$C_{Nano}$ was prepared at 30 nM in 30 ul volume while the BoNT/B was diluted from 10 nM to 1 fM with factor 10. The negative control was BoNT/A added in the sensor protein solution. The curve (FIG. 3A) was plotted based on the percentage of luminescence of NANOLUC™ luciferase. EC 50 for BoNT/B is 75.7 pM after 4 h and 3.9 pM after 24 h at 37° C. (FIG. 3B).

Figure 4:
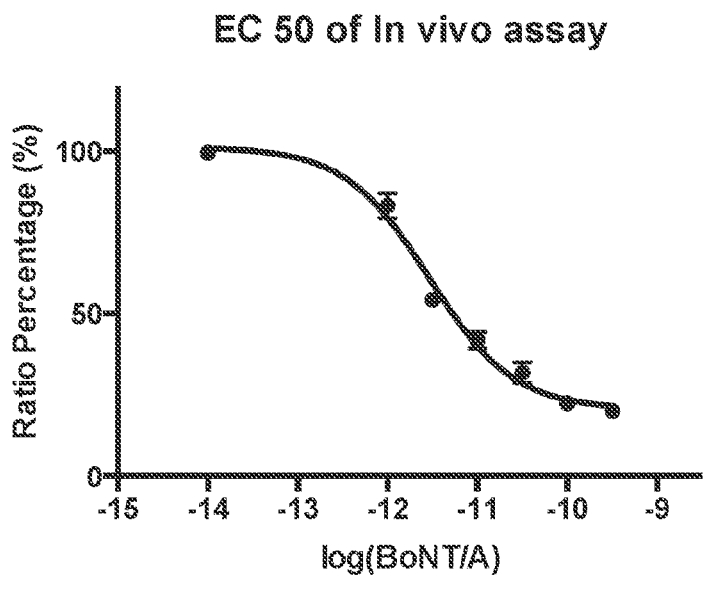

FIG. 4 demonstrates an in vivo detection assay of BoNT/A using virus infected neurons cells. For each neuron cell lysate sample, both Firefly and NANOLUC™ luciferase signals were measured and the ratio (NANOLUC™/Firefly) was calculated. Afterwards, the percentage of each sample's ratio was generated using no toxin exposure as reference control. The EC50=2.9 pM equal to 30 fold of LD50 after 48 h challenged with toxin proteins.

DETAILED DESCRIPTION

Figure 1:
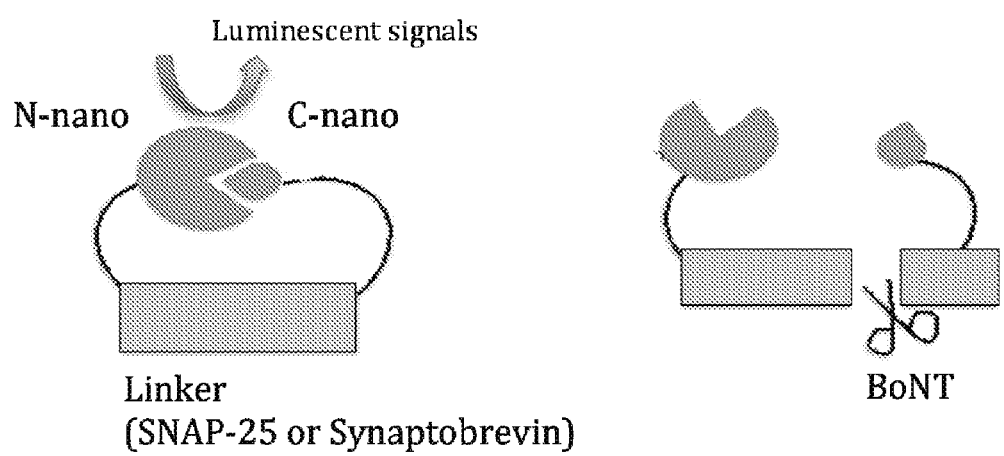
FIG. 1 depicts a schematic drawing of split luciferase based toxin sensors. Left panel: NANOLUC™ luciferase is separated into two complementary fragments, N-nano and C-nano. These two fragments are linked together with a linker that is based on toxin substrates (SNAP-25 (also known as p25) or VAMP1/2/3 (e.g., synaptobrevins)). Right panel: Cleavage of the linker region by BoNTs separates the two parts of NANOLUC™ luciferase and abolishes the luminescent signals.

Described herein are compositions and methods relating to measuring and/or detecting enzymatic activity. In particular, the compositions and methods relate to the detection and/or measurement of neurotoxins, e.g., *C. botulinum* neurotoxin (BoNT).

As used herein, "*C. botulinum* neurotoxin" or "BoNT" refers to any polypeptide that can execute the overall cellular mechanism whereby a *C. botulinum* toxin enters a neuron and inhibits neurotransmitter release and encompasses the binding of a *C. botulinum* toxin to a low or high affinity receptor complex, the internalization of the toxin, the translocation of the toxin light chain into the cytoplasm and the enzymatic modification of a *C. botulinum* toxin substrate.

Strains of *Clostridium botulinum* produce seven antigenically-distinct types of Botulinum toxins (BoNTs), which have been identified by investigating botulism outbreaks in man (BoNT/A, /B, /E and/F), animals (BoNT/C1 and/D), or isolation from soil (BoNT/G). While all seven BoNT serotypes have similar structure and pharmacological properties, each also displays heterogeneous bacteriological characteristics. The genetic diversity of the *C. botulinum* strains is described in detail in Hill et al. (Journal of Bacteriology, Vol. 189, No. 3, p. 818-832 (2007)), the contents of which are incorporated herein by reference. In some embodiments of any of the aspects described herein, the BoNT is of strain A, E, C, B, D, F or G. Various non-naturally occurring *C. botulinum* neurotoxins are also known in the art and described, e.g., in International Patent Publications WO95/32738, WO96/33273, WO98/07864 and WO99/17806, each of which is incorporated herein by reference.

Toxins from the various *C. botulinum* strains share the same functional domain organization and overall structural architecture. *C. botulinum* toxins are each translated as a single chain polypeptide of approximately 150 kDa that is subsequently cleaved by proteolytic scission within a disulfide loop by a naturally-occurring proteases, such as, e.g., an endogenous *C. botulinum* toxin protease or a naturally-occurring proteases produced in the environment. This post-translational processing yields a di-chain molecule comprising an approximately 50 kDa light chain (LC) and an approximately 100 kDa heavy chain (HC) held together by a single disulfide bond and noncovalent interactions. Each mature di-chain molecule comprises three functionally distinct domains: 1) a proteolytic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC that determines the binding activity and binding specificity of the toxin to the receptor complex located at the surface of the target cell.

The binding, translocation and protease activity of these three functional domains are all necessary for toxicity. The overall cellular intoxication mechanism whereby *C. botulinum* toxins enter a neuron and inhibit neurotransmitter release is similar, regardless of serotype or subtype. Without wishing to be bound by theory, the intoxication mechanism involves at least four steps: 1) receptor binding, 2) complex internalization, 3) light chain translocation, and 4) protease target modification. The process is initiated when the $H_C$ domain of a *C. botulinum* toxin binds to a toxin-specific receptor located on the plasma membrane surface of a target cell. The binding specificity of a receptor complex is thought to be achieved, in part, by specific combinations of gangliosides and protein receptors. Once bound, the toxin/receptor complexes are internalized by endocytosis and the internalized vesicles are sorted to specific intracellular routes. The translocation step is triggered by the acidification of the vesicle compartment. Once translocated, light chain endopeptidase of the toxin is released from the intracellular vesicle into the cytosol where it specifically targets one of three proteins known as the core components of the neurotransmitter release apparatus (vesicle-associated membrane protein (VAMP)/synaptobrevin, synaptosomal-associated protein of 25 kDa (SNAP-25) and Syntaxin).

These core components are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic plasma membrane surface. The selective proteolysis of synaptic SNAREs accounts for the block of neurotransmitter release caused by *C. botulinum* toxins in vivo. The SNARE protein targets of *C. botulinum* toxins are common to exocytosis in a variety of non-neuronal types; in these cells, as in neurons, light chain peptidase activity inhibits exocytosis, see, e.g., Yann Humeau et al., How Botulinum and Tetanus Neurotoxins Block Neurotransmitter Release, 82(5) Biochimie. 427-446 (2000); Kathryn Turton et al., Botulinum and Tetanus Neurotoxins: Structure, Function and Therapeutic Utility, 27(11) Trends Biochem. Sci. 552-558. (2002); Giovanna Lalli et al., The Journey of Tetanus and Botulinum Neurotoxins in Neurons, 11(9) Trends Microbiol. 431-437, (2003).

Described herein are single chain polypeptides in which a reporter protein is split or interrupted in its sequence by a linker segment. The split reporter protein is functional.

As used herein, the term "single chain" when referring to a polypeptide refers to a single polypeptide molecule having a series of amino acid residues, connected to each other by peptide bonds between the alpha-amino and carboxy groups of adjacent residues. That is, each recited element of a single chain polypeptide is connected to the other element(s) by means of a peptide bond. This is in contrast to multi-chain polypeptides which comprise multiple single chain polypeptides which can bind to each other via, e.g., hydrogen bonding or disulfide bonds to form a polypeptide complex.

The single chain polypeptides described herein can comprise luciferase and/or portions thereof, e.g., the reporter protein can be luciferase. As used herein, "luciferase" refers to an enzyme that catalyzes a bioluminescent reaction, e.g., by catalyzing the oxidation of luciferin, emitting light and releasing oxyluciferin. A luciferase can be naturally-occurring or engineered. As used herein, a "functional" luciferase is a luciferase that is capable of catalyzing a reaction in the presence of a suitable substrate. Numerous variations and embodiments of luciferase are available, including, e.g., firefly luciferase (*Photinus pyralis*) (see, e.g, SEQ ID NO: 13), bacterial luciferase (*Vibrio fischeri, Vibrio harveyi*), sea pansy luciferase (*Renilla reniformis*), dinoflagellate luciferase, *Cypridina* luciferase, *Coleoptera* luciferase, *Gaussia* luciferase (see, e.g., Heise, K., et al, "Dual luciferase assay for secreted luciferase based on *Gaussia* and NANOLUC" Assay Drug Dev. Technol. (2013); which is incorporated by reference herein in its entirety), copepod luciferase (see, e.g., Takenaka, Y., et al, "Computational analysis and functional expression of ancestral copepod luciferase" Gene (2013); which is incorporated by reference herein in its entirety) and NANOLUC™ luciferase.

In some embodiments of any of the aspects described herein, the luciferase can be NANOLUC™ luciferase. As used herein, "NANOLUC luciferase" refers to a 19.1 kDa luciferase derived from *Oplophorus gracilirostris* luciferase that can utilize furimazine or coelenterazine as a substrate and which has the sequence of SEQ ID NO: 1. Variants of NANOLUC™ luciferase can also be used in any of the aspects and embodiments of the methods and compositions herein and are described, e.g., in U.S. Pat. No. 8,557,970; which is incorporated by reference herein in its entirety.

In one aspect of any of the embodiments, described herein is a single chain polypeptide comprising, from N-terminal to C-terminal: a N-terminal fragment of a reporter protein; a linker comprising a neurotoxin cleavage site; and a C-terminal fragment of the reporter protein. As used herein, "fragment" refers to a part or portion of a molecule, e.g., a part or portion of a polypeptide. In the single chain polypeptides described herein, the N-terminal fragment and C-terminal fragments of a reporter protein collectively comprise a functional reporter protein sequence but do not individually comprise a functional reporter protein sequence. When present in the same single chain polypeptide, e.g., joined functionally by the linker sequence, the N-terminal and C-terminal fragments of a reporter protein generate a functional reporter fusion protein. In some embodiments of any of the aspects, the reporter protein is a luciferase protein. In some embodiments of any of the aspects, the fragments can be variants or derivatives of naturally-occurring sequences, reporter protein sequences described herein, and/or reporter protein sequences known in the art, e.g., they can have at least 90% sequence identity to a reporter protein sequence or have no more than 10 amino acid residue substitutions, deletions, or additions relative to a reporter protein sequence.

In one aspect of any of the embodiments, described herein is a single chain polypeptide comprising a N-terminal domain comprising a sequence with at least 90% sequence identity to amino acids 1-159 of the luciferase of SEQ ID NO 1 (N-nano$_{1-159}$); a linker comprising a neurotoxin cleavage site located C-terminal to the N-nano$_{1-159}$, and a C-terminal domain having a sequence with at least 90% sequence identity amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In some embodiments of any of the aspects, a domain or fragment of a reporter protein can have at least at least 90%, at least 95%, or at least 98% sequence identity with a reporter protein sequence, e.g., with amino acids 1-159 of the luciferase of SEQ ID NO: 1 (N-nano$_{1-159}$) or amino acids 160-170 of the luciferase of SEQ ID NO: 1 (C-nano$_{160-170}$). In some embodiments of any of the aspects, the variant amino acids can be conservative substitution variations.

In one aspect of any of the embodiments, described herein is a single chain polypeptide comprising: a N-terminal domain comprising a sequence having less than 10 amino acid residues substitutions, deletions, or additions relative to amino acids 1-159 of the luciferase of SEQ ID NO: 1 (N-nano$_{1-159}$); a linker comprising a neurotoxin cleavage site located C-terminal to the N-nano$_{1-159}$ and a C-terminal domain having a sequence having less than 3 amino acid residues substitutions, deletions, or additions relative to amino acids 160-170 of the luciferase of SEQ ID NO: 1 (C-nano$_{160-170}$) located C-terminal to the linker; wherein the linker functionally joins the N-nano$_{1-159}$ and the C-nano$_{160-170}$ to generate a functional luciferase fusion protein.

In some embodiments of any of the aspects, a domain or fragment of a reporter protein can be a sequence with 10 or less, 9 or less, 8 or less, 7 or less, 6 or less, 5 or less, 4 or less, 3 or less, 2 or less, or 1 deletions, insertions, or substitutions relative to a reporter protein sequence, e.g., to amino acids 1-159 of the luciferase of SEQ ID NO: 1 (N-nano$_{1-159}$) or amino acids 160-170 of the luciferase of SEQ ID NO: 1 (C-nano$_{160-170}$). In some embodiments of any of the aspects, the substituted amino acids can be conservative substitution variations. In one aspect of any of the embodiments, described herein is a single chain polypeptide comprising: a) amino acids 1-159 of NANOLUC™ luciferase (N-nano$_{1-159}$); b) a linker comprising a neurotoxin cleavage site located C-terminal to the N-nano$_{1-159}$; and c) amino acids 160-170 of NANOLUC™ luciferase (C-nano$_{160-170}$) located C-terminal to the linker; wherein the linker functionally joins the N-nano$_{1-159}$ and the C-nano$_{160-170}$ to generate a functional luciferase fusion protein.

As demonstrated herein, a luciferase protein can be interrupted by a linker sequence while still providing a functional luciferase. In some embodiments of any of the aspects described herein, a linker is provided between residues corresponding to residues 159 and 160 of SEQ ID NO: 1. In some embodiments of any of the aspects described herein, a linker is provided between residues 159 and 160 of SEQ ID NO: 1.

In some embodiments of any of the aspects described herein, a single chain polypeptide as described herein can comprise an N-terminal domain comprising a sequence corresponding to residues 1-159 of SEQ ID NO: 1 and a C-terminal domain comprising a sequence corresponding to residues 160-170 of SEQ ID NO: 1. In some embodiments of any of the aspects described herein, a single chain polypeptide as described herein can comprise an N-terminal domain consisting essentially of a sequence corresponding to residues 1-159 of SEQ ID NO: 1 and a C-terminal domain consisting essentially of a sequence corresponding to residues 160-170 of SEQ ID NO: 1.

In some embodiments of any of the aspects described herein, a single chain polypeptide as described herein can comprise an N-terminal domain comprising residues 1-159 of SEQ ID NO: 1 and a C-terminal domain comprising residues 160-170 of SEQ ID NO: 1. In some embodiments of any of the aspects described herein, a single chain polypeptide as described herein can comprise an N-terminal domain consisting essentially of residues 1-159 of SEQ ID NO: 1 and a C-terminal domain consisting essentially of residues 160-170 of SEQ ID NO: 1. In some embodiments of any of the aspects described herein, a single chain polypeptide as described herein can comprise an N-terminal domain consisting of residues 1-159 of SEQ ID NO: 1 and a C-terminal domain consisting of residues 160-170 of SEQ ID NO: 1.

In the single chain polypeptides described herein, a linker domain is found between the N-terminal and C-terminal domains. As used herein, "linker" refers to a sequence exogenous to a reporter protein (e.g. a luciferase enzyme) and which is engineered to functionally join the N-terminal and C-terminal domains of the reporter protein. A linker can comprise, e.g., one or more cleavage sites, one or more spacers, one or more binding fragments, and one or more additional luciferase enzymes.

As used herein, "functionally join" refers to joining the two fragments of a reporter protein, e.g., a luciferase in such a way that the intervening sequence does not prevent the two fragments from forming an active and functional tertiary structure. Two fragments which are functionally joined will exhibit the activity which characterizes the protein in the absence of the linker sequence.

In some embodiments of any of the aspects described herein, a linker can comprise one or more cleavage sites, e.g., an amino acid sequence which is specifically cleaved by the action of one or more enzymes. In some embodiments of any of the aspects described herein, the cleavage site can be a neurotoxin cleavage site. Accordingly, a neurotoxin cleavage site comprises a sequence which is specifically cleaved by at least one neurotoxin. Neurotoxins are compounds which inhibit the function of and/or kill nervous tissue. In some embodiments of any of the aspects described herein, the neurotoxin can be an inhibitor of synaptic vesicle release. Exemplary non-limiting neurotoxin cleavage sites can include a *C. botulinum* neurotoxin (BoNT) and/or a Tetanus neurotoxin cleavage site. In some embodiments of any of the aspects described herein, a linker can comprise multiple neurotoxin cleavage sites, e.g., it can be cleaved by multiple neurotoxins, thereby permitting the detection and/or measurement of multiple neurotoxins.

BoNT acts by cleaving SNARE proteins. Accordingly, a BoNT cleavage site can be from a SNARE protein. As used herein, "SNARE protein" refers to a superfamily of proteins that mediate vesicle fusion, including fusion of synaptic vesicles of the presynaptic membrane in neurons. SNARE proteins include, by way of non-limiting examples, SNAP-25 (e.g., NCBI Gene ID: 6616, see also NCBI Reference Sequence: NP_570824.1 for human SNAP25b and NCBI Reference Sequence: NP_112253.1 for rat SNAP25b), synaptobrevins (VAMPs)(e.g., NCBI Gene ID Nos: 6843; 6844; 6845; 8673; 8674; 9341; 9554; 10652; 10791; and 26984) and syntaxins (e.g., NCBI Gene ID Nos. 2054; 6804; 6809; 6810; 6811; 8417; 8675; 8676; 8677; 9482; 10228; 23673; 53407; 55014; 112755; and 415177). SNARE scissile bonds cleaved by clostridial neurotoxins are described for example in Binz, Th. et al. "Clostridial neurotoxins: mechanism of SNARE cleavage and outlook on potential substrate specificity reengineering." Toxins 2.4 (2010): 665-682. Preferably, the BoNT cleavage site is from a human SNARE protein. Examples of human SNARE scissile bonds are provided in Table 1.

TABLE 1 human SNARE scissile bonds cleaved by clostridial neurotoxins

| Neurotoxin | SNARE | Scissile bond |
|---|---|---|
| BoNT/A | SNAP25 (SEQ ID NO: 23). | Gln197-Arg198 |
| BoNT/B | VAMP-1 (SEQ ID NO: 24). | Gln78-Phe79 |
|  | VAMP-2 (SEQ ID NO: 25). | Gln76-Phe77 |
|  | VAMP-3 (SEQ ID NO: 26). | Gln59-Phe60 |
| BoNT/C1 | SNAP25 (SEQ ID NO: 23). | Arg198-Ala199 |
|  | Syntaxin 1A (SEQ ID NO: 27). | Lys253-Ala254 |
|  | Syntaxin 1B (SEQ ID NO: 28). | Lys252-Ala253 |
| BoNT/D | VAMP-1 (SEQ ID NO: 24). | Lys61-Leu62 |
|  | VAMP-2 (SEQ ID NO: 25). | Lys59-Leu60 |
|  | VAMP-3 (SEQ ID NO: 26). | Lys42-Leu43 |
| BoNT/E | SNAP25 (SEQ ID NO: 23). | Arg180-Ile181 |
| BoNT/F | VAMP-1 (SEQ ID NO: 24). | Gln60-Lys61 |
|  | VAMP-2 (SEQ ID NO: 25). | Gln58-Lys59 |
|  | VAMP-3 (SEQ ID NO: 26). | Gln41-Lys42 |
| BoNT/G | VAMP-1 (SEQ ID NO: 24). | Ala83-Ala84 |
|  | VAMP-2 (SEQ ID NO: 25). | Ala81-Ala82 |
|  | VAMP-3 (SEQ ID NO: 26). | Ala64-Ala65 |
| TeNT | VAMP-1 (SEQ ID NO: 24). | Gln78-Phe79 |
|  | VAMP-2 (SEQ ID NO: 25). | Gln76-Phe77 |
|  | VAMP-3 (SEQ ID NO: 26). | Gln59-Phe60 |

In one embodiment, the linker comprises at least one clostridial neurotoxin cleavage site, preferably a human neurotoxin cleavage site. A clostridial neurotoxin cleavage site may be defined as a sequence comprising at least amino acid residues P3P2P1P1'P2'P3' of a SNARE, preferably a human SNARE, wherein P1 and P1' are the residues located on either side of the scissile peptide bond cleaved by the clostridial neurotoxin, for example Gln197 and Arg198 in human SNAP25 for BoNT/A.

In a preferred embodiment, a clostridial neurotoxin cleavage site comprises at least amino acid residues P4P3P2P1P1'P2'P3'P4' of the SNARE. In a more preferred embodiment, a clostridial neurotoxin cleavage site comprises at least amino acid residues P5P4P3P2P1P1'P2'P3'P4'P5' of the SNARE, more preferably at least amino acid residues P6P5P4P3P2P1P1'P2'P3'P4'P5'P6'.

In one embodiment, the linker comprises at least one BoNT/A cleavage site wherein said BoNT/A cleavage site comprises residues 195 to 200, preferably 194 to 201, 193 to 202 or 192 to 203 of human SNAP25 (SEQ ID NO: 23).

In one embodiment, the linker comprises at least one BoNT/B cleavage site wherein said BoNT/B cleavage site comprises residues 76 to 81, preferably 75 to 82, 74 to 83 or 73 to 84 of human VAMP-1 (SEQ ID NO: 24).

In one embodiment, the linker comprises at least one BoNT/B cleavage site wherein said BoNT/B cleavage site comprises residues 74 to 79, preferably 73 to 80, 72 to 81 or 71 to 82 of human VAMP-2 (SEQ ID NO: 25).

In one embodiment, the linker comprises at least one BoNT/B cleavage site wherein said BoNT/B cleavage site comprises residues 57 to 62, preferably 56 to 63, 55 to 64 or 54 to 65 of human VAMP-3 (SEQ ID NO: 26).

In one embodiment, the linker comprises at least one BoNT/C1 cleavage site wherein said BoNT/C1 cleavage site comprises residues 196 to 201, preferably 195 to 202, 194 to 203 or 193 to 204 of human SNAP25 (SEQ ID NO: 23).

In one embodiment, the linker comprises at least one BoNT/C1 cleavage site wherein said BoNT/C1 cleavage site comprises residues 251 to 256, preferably 250 to 257, 249 to 258 or 148 to 259 of human Syntaxin 1A (SEQ ID NO: 27).

In one embodiment, the linker comprises at least one BoNT/C1 cleavage site wherein said BoNT/C1 cleavage site comprises residues 252 to 257, preferably 251 to 258, 249 to 259 or 149 to 260 of human Syntaxin 1B (SEQ ID NO: 28).

In one embodiment, the linker comprises at least one BoNT/D cleavage site wherein said BoNT/D cleavage site comprises residues 59 to 64, preferably 58 to 65, 57 to 66 or 56 to 67 of human VAMP-1 (SEQ ID NO: 24).

In one embodiment, the linker comprises at least one BoNT/D cleavage site wherein said BoNT/D cleavage site comprises residues 57 to 62, preferably 56 to 63, 55 to 64 or 54 to 65 of human VAMP-2 (SEQ ID NO: 25).

In one embodiment, the linker comprises at least one BoNT/D cleavage site wherein said BoNT/D cleavage site comprises residues 40 to 45, preferably 39 to 46, 38 to 47 or 37 to 48 of human VAMP-3 (SEQ ID NO: 26).

In one embodiment, the linker comprises at least one BoNT/E cleavage site wherein said BoNT/E cleavage site comprises residues 178 to 183, preferably 177 to 184, 176 to 185 or 175 to 186 of human SNAP25 (SEQ ID NO: 23).

In one embodiment, the linker comprises at least one BoNT/F cleavage site wherein said BoNT/F cleavage site comprises residues 58 to 63, preferably 57 to 64, 56 to 65 or 55 to 66 of human VAMP-1 (SEQ ID NO: 24).

In one embodiment, the linker comprises at least one BoNT/F cleavage site wherein said BoNT/F cleavage site comprises residues 56 to 61, preferably 55 to 62, 54 to 63 or 53 to 64 of human VAMP-2 (SEQ ID NO: 25).

In one embodiment, the linker comprises at least one BoNT/F cleavage site wherein said BoNT/F cleavage site comprises residues 39 to 44, preferably 38 to 45, 37 to 46 or 36 to 47 of human VAMP-3 (SEQ ID NO: 26).

In one embodiment, the linker comprises at least one BoNT/G cleavage site wherein said BoNT/G cleavage site comprises residues 81 to 86, preferably 80 to 87, 79 to 88 or 78 to 89 of human VAMP-1 (SEQ ID NO: 24).

In one embodiment, the linker comprises at least one BoNT/G cleavage site wherein said BoNT/G cleavage site comprises residues 79 to 84, preferably 78 to 85, 77 to 86 or 76 to 87 of human VAMP-2 (SEQ ID NO: 25).

In one embodiment, the linker comprises at least one BoNT/G cleavage site wherein said BoNT/G cleavage site comprises residues 62 to 67, preferably 61 to 68, 60 to 69 or 59 to 70 of human VAMP-3 (SEQ ID NO: 26).

In one embodiment, the linker comprises at least one BoNT/B cleavage site wherein said TeNT cleavage site comprises residues 76 to 81, preferably 75 to 82, 74 to 83 or 73 to 84 of human VAMP-1 (SEQ ID NO: 24).

In one embodiment, the linker comprises at least one TeNT cleavage site wherein said TeNT cleavage site comprises residues 74 to 79, preferably 73 to 80, 72 to 81 or 71 to 82 of human VAMP-2 (SEQ ID NO: 25).

In one embodiment, the linker comprises at least one TeNT cleavage site wherein said BoNT/B cleavage site comprises residues 57 to 62, preferably 56 to 63, 55 to 64 or 54 to 65 of human VAMP-3 (SEQ ID NO: 26).

An example of suitable BoNT cleavage sites in SNARE proteins include, by way of non-limiting example, amino acids 141-206 of human SNAP-25b (e.g., SEQ ID NO: 10); and amino acid 35-96 of human VAMP1 (e.g., NCBI Gene ID: 6843). In some embodiments of any of the aspects described herein, amino acids of 35-96 of human VAMP1 can be amino acids 35-96 of SEQ ID NO: 16. Further non-limiting examples of BoNT cleavage sites in SNARE proteins include amino acids 60-87 of human VAMP2, amino acids 43-70 of human VAMP 3, and amino acids 62-89 of human VAMP1. In some embodiments of any of the aspects, amino acids 60-87 of human VAMP2 can be the sequence of SEQ ID NO: 19. In some embodiments of any of the aspects, amino acids 43-70 of human VAMP3 can be the sequence of SEQ ID NO: 20. In some embodiments of any of the aspects, amino acids 62-89 of human VAMP1 can be the sequence of SEQ ID NO: 21

In some embodiments of any of the aspects, a BoNT cleavage site can be a variant of any of the specific sequences recited herein, e.g., a variant of a native BoNT cleavage site found in a SNARE protein. In some embodiments of any of the aspects, a BoNT cleavage site can be a variant of amino acids 141-206 of SEQ ID NO: 10 or amino acids 35-96 of SEQ ID NO: 16. In some embodiments of any of the aspects, a BoNT cleavage site can have at least 80%, at least 85%, at least 90%, at least 95%, or at least 98% sequence identity with a native BoNT cleavage site found in a SNARE protein. In some embodiments of any of the aspects, a BoNT cleavage site can have at least 80%, at least 85%, at least 90%, at least 95%, or at least 98% sequence identity with amino acids 141-206 of SEQ ID NO: 10 or amino acids 35-96 of SEQ ID NO: 16. In some embodiments of any of the aspects, the variant can be a conservative substitution variant.

In some embodiments of any of the aspects, a BoNT cleavage site can be a sequence with 10 or less, 9 or less, 8 or less, 7 or less, 6 or less, 5 or less, 4 or less, 3 or less, 2 or less, or 1 deletions, insertions, or substitutions relative to a native BoNT cleavage site found in a SNARE protein. In some embodiments of any of the aspects, a BoNT cleavage site can be a sequence with 10 or less, 9 or less, 8 or less, 7 or less, 6 or less, 5 or less, 4 or less, 3 or less, 2 or less, or 1 residues which vary relative to a native BoNT cleavage site found in a SNARE protein. In some embodiments of any of the aspects, a BoNT cleavage site can be a sequence with 10 or less, 9 or less, 8 or less, 7 or less, 6 or less, 5 or less, 4 or less, 3 or less, 2 or less, or 1 deletion, insertion, or substitution relative to amino acids 141-206 of SEQ ID NO: 10 or amino acids 35-96 of SEQ ID NO: 16. In some embodiments of any of the aspects, a BoNT cleavage site can be a sequence with 10 or less, 9 or less, 8 or less, 7 or less, 6 or less, 5 or less, 4 or less, 3 or less, 2 or less, or 1 residues which vary relative to with amino acids 141-206 of SEQ ID NO: 10 or amino acids 35-96 of SEQ ID NO: 16.

In some embodiments of any of the aspects described herein, a BoNT cleavage site can comprise amino acids 141-206 of human SNAP-25b (e.g., SEQ ID NO: 10); amino acid 35-96 of human VAMP1; amino acids 1-96 of VAMP1; human SNAP25; and/or amino acids 1-206 of human SNAP25b (SEQ ID NO: 14).

In some embodiments of any of the aspects described herein, a BoNT cleavage site can be specifically recognized (e.g. cleaved) by BoNT A, B, C, D, E, F, and/or G. In some embodiments of any of the aspects described herein, a BoNT cleavage site can be specifically recognized (e.g. cleaved) by BoNT A, E and C. In some embodiments of any of the aspects described herein, a BoNT cleavage site can be specifically recognized (e.g. cleaved) by BoNT B, D, F and G.

In some embodiments of any of the aspects described herein, a linker can comprise one or more spacers. As used herein, "spacer" refers to an amino acid sequence that serves the structural purpose of separating two other sequences in the same peptide chain. In some embodiments of any of the aspects described herein, the spacer sequence can be a flexible peptide sequence. In some embodiments of any of the aspects described herein, a spacer can comprise glycine and serine residues. In some embodiments of any of the aspects described herein, a spacer can consist essentially of glycine and serine residues. In some embodiments of any of the aspects described herein, a spacer can consist of glycine and serine residues.

In some embodiments of any of the aspects described herein, a spacer can be from about 2 to about 30 amino acids in length. In some embodiments of any of the aspects described herein, a spacer can be from 2 to 30 amino acids in length. In some embodiments of any of the aspects described herein, a spacer can be from about 3 to about 20 amino acids in length. In some embodiments of any of the aspects described herein, a spacer can be from 3 to 20 amino acids in length. In some embodiments of any of the aspects described herein, a spacer can be from about 5 to about 15 amino acids in length. In some embodiments of any of the aspects described herein, a spacer can be from 5 to 15 amino acids in length.

Exemplary, non-limiting spacers can include GSSGGGGSGGGGSSG (SEQ ID NO: 4); GSSGGGGSGGGSSG (SEQ ID NO: 5); GGGGS (SEQ ID NO: 6); (GGGGS)n (n=1-3) (SEQ ID NO: 7); KES-GSVSSEQLAQFRSLD (SEQ ID NO: 8); and EGKSSGSGSESKST (SEQ ID NO: 9). Linker design, selection, and further exemplary linkers are well-known in the art and described, e.g., in Chen, X., et al, "Fusion protein linkers: proterty, design and functionality" Adv. Drug Deliv. Rev. (2013); which is incorporated by reference herein in its entirety.

In some embodiments of any of the aspects described herein, a linker can comprise a neurotoxin binding fragment, e.g., a sequence that is bound by and/or binds to a neurotoxin and which is not cleaved by the neurotoxin. In some embodiments of any of the aspects described herein, a neurotoxin binding fragment can be a fragment of a neurotoxin receptor, e.g., a receptor for the BoNT and/or a tetanus neurotoxin.

In some embodiments of any of the aspects described herein, the neurotoxin receptor can be a human, mouse, rat, or primate neurotoxin receptor. In a preferred embodiment, the neurotoxin receptor is a human neurotoxin receptor. In some embodiments of any of the aspects described herein, the neurotoxin receptor can be SV2C, e.g., human SV2C (NCBI Gene ID: 22987; GenBank: AAI00828.1). In some embodiments of any of the aspects described herein, the neurotoxin binding fragment of a receptor can comprise a sequence corresponding to amino acids 529-566 of human SV2C (SV2C-L4, e.g., SEQ ID NO: 11). In some embodiments of any of the aspects described herein, the neurotoxin binding fragment can comprise amino acids 529-566 of human SV2C (SV2C-L4, e.g., SEQ ID NO: 11). In some embodiments of any of the aspects described herein, the neurotoxin receptor can be SYTI (NCBI Gene ID: 6857) or SYT2 (NCBI Gene ID: 127833). In some embodiments of any of the aspects described herein, the neurotoxin binding fragment of a receptor can comprise a sequence corresponding to amino acids 32-52 of SYTI (e.g., SEQ ID NO: 17) or amino acids 40-60 of SYT2 (SEQ ID NO: 18).

In some embodiments of any of the aspects described herein, a linker can comprise an intact second luciferase polypeptide. In some embodiments of any of the aspects described herein, the second luciferase is active before and/or after cleavage of the single chain polypeptide, e.g. by a neurotoxin. In some embodiments of any of the aspects described herein, the second luciferase is distinguishable from the first luciferase, e.g. it acts on a different substrate and/or produces a different wavelength of light. For example, if the first luciferase is NANOLUC, the second luciferase can be firefly luciferase (e.g., *Photinus pyrahs*), bacterial luciferase (e.g., *Vibrio fischieri, Vibrio harveyi*), sea pansy luciferase (e.g., *Renilla reniformis*), dinoflagellate luciferase, or *Gaussia* luciferase. In some embodiments of any of the aspects described herein, the second luciferase can comprise a sequence corresponding to SEQ ID NO: 13. In some embodiments of any of the aspects described herein, the second luciferase can comprise SEQ ID NO: 13.

In some embodiments of any of the aspects described herein, a linker can comprise an intact second luciferase polypeptide located between the N-terminal reporter protein domain and at least one cleavage site. In some embodiments of any of the aspects described herein, a linker can comprise an intact second luciferase polypeptide located between the N-nano$_{1-159}$ and the BoNT cleavage site.

In some embodiments of any of the aspects described herein, the binding fragment can be located N-terminal of at least one cleavage site. In some embodiments of any of the aspects described herein, the binding fragment can be located between the N-nano$_{1-159}$ and the BoNT cleavage site. In some embodiments of any of the aspects described herein, the linker can comprise, from N-terminal to C-terminal, at least one binding fragment, at least one spacer, and at least one cleavage site. In some embodiments of any of the aspects described herein, the linker can comprise, from N-terminal to C-terminal, at least one binding fragment, at least one spacer, and at least one BoNT cleavage site.

In some embodiments of any of the aspects described herein, a linker can comprise, from N-terminus to C-terminus, one or more spacers and at least one cleavage site. In some embodiments of any of the aspects described herein, a linker can comprise, from N-terminus to C-terminus, one or more spacers, at least one cleavage site, and one or more spacers. In some embodiments of any of the aspects described herein, a linker can comprise, from N-terminus to C-terminus, at least one cleavage site, and one or more spacers. In some embodiments of any of the aspects described herein, a linker can comprise one or more spacers located between the BoNT cleavage site and the N-nano$_{1-159}$, between the neurotoxin cleavage site and the C-nano$_{160-170}$, or a combination thereof.

In some embodiments of any of the aspects described herein, the linker can comprise a spacer located between a second luciferase polypeptide and a cleavage site. In some embodiments of any of the aspects described herein, the linker can comprise, from N-terminal to C-terminal, a second luciferase polypeptide, at least one spacer, and at least one cleavage site. In some embodiments of any of the aspects described herein, the linker can comprise a spacer located between the second luciferase polypeptide and the BoNT cleavage site.

In some embodiments of any of the aspects described herein, the single chain polypeptide can further comprise a polyhistidine affinity tag, e.g., His6 (SEQ ID NO: 12). In some embodiments of any of the aspects described herein, the polyhistidine affinity tag is located at the C-terminus of the polypeptide, e.g., C-terminal of the reporter protein C-terminal domain.

In one aspect of any of the embodiments, described herein is a single chain polypeptide comprising: a) amino acids 1-159 of NANOLUC™ luciferase (N-nano$_{1-159}$); b) a linker located C-terminal to the N-nano$_{1-159}$ comprising: i) a first spacer of 5 to 15 amino acids; ii) a binding fragment comprised of amino acids 529-566 of SV2C located C-terminal to the first spacer; iii) a second spacer located C-terminal to the binding fragment; iv) a BoNT cleavage site comprising amino acids 141-206 of human SNAP25b located C-terminal to the second spacer; iv) a third spacer of 5 to 15 amino acids located C-terminal to the BoNT cleavage site; and c) amino acids 160-170 of NANOLUC™ luciferase (C-$nano_{160-170}$ located C-terminal to the linker; wherein the linker functionally joins the N-$nano_{1-159}$ and the C-$nano_{160-170}$ to generate a functional luciferase fusion protein. In some embodiments of any of the aspects described herein, the polypeptide further comprises a polyhistidine affinity tag C-terminal of the amino acids 160-170 of NANOLUC™ luciferase (C-$nano_{160-170}$).

In one aspect of any of the embodiments, described herein is a single chain polypeptide comprising: a) amino acids 1-159 of NANOLUC™ luciferase (N-$nano_{1-159}$); b) a linker located C-terminal to the N-$nano_{1-159}$ comprising: i) a first spacer from 5 to 15 amino acids; ii) a BoNT cleavage site comprising amino acids 141-206 of human SNAP25b located C-terminal to the first spacer; iii) a second spacer of 5 to 15 amino acids located C-terminal to the BoNT cleavage site; and c) amino acids 160-170 of NANOLUC™ luciferase (C-$nano_{160-170}$) located C-terminal to the linker; wherein the linker functionally joins the N-$nano_{1-159}$ and the C-$nano_{160-170}$ to generate a functional luciferase fusion protein. In some embodiments of any of the aspects described herein, the polypeptide further comprises a polyhistidine affinity tag C-terminal of the amino acids 160-170 of NANOLUC™ luciferase (C-$nano_{160-170}$.

In one aspect of any of the embodiments, described herein is a single chain polypeptide comprising: a) amino acids 1-159 of NANOLUC™ luciferase (N-$nano_{1-159}$); b) a linker located C-terminal to the N-$nano_{1-159}$ comprising: i) a first spacer of 5 to 15 amino acids; ii) a BoNT cleavage site comprising amino acids 35-96 of human VAMP1 located C-terminal to the first spacer; iii) a second spacer of 5 to 15 amino acids located C-terminal to the BoNT cleavage site; and c) amino acids 160-170 of NANOLUC™ luciferase (C-$nano_{160-170}$) located C-terminal to the linker; wherein the linker functionally joins the N-$nano_{1-159}$ and the C-$nano_{160-170}$ to generate a functional luciferase fusion protein. In some embodiments of any of the aspects described herein, the polypeptide further comprises a polyhistidine affinity tag C-terminal of the amino acids 160-170 of NANOLUC™ luciferase (C-$nano_{160-170}$).

In one aspect of any of the embodiments, described herein is a single chain polypeptide comprising: a) amino acids 1-159 of NANOLUC™ luciferase (N-$nano_{1-159}$); b) a linker located C-terminal to the N-$nano_{1-159}$ comprising: i) a second functional luciferase polypeptide; ii) a first spacer of 5 to 15 amino acids located C-terminal of the second luciferase polypeptide; iii) a BoNT cleavage site comprising amino acids 1-206 of human SNAP25b (e.g. SEQ ID NO: 14) located C-terminal to the first spacer; iv) a second spacer of 5 to 15 amino acids located C-terminal to the BoNT cleavage site; and c) amino acids 160-170 of NANOLUC™ luciferase (C-$nano_{160-170}$) located C-terminal to the linker; wherein the linker functionally joins the N-$nano_{1-159}$ and the C-$nano_{160-170}$ to generate a functional luciferase fusion protein.

In some embodiments of any of the aspects described herein, the polypeptide further comprises a polyhistidine affinity tag C-terminal of the amino acids 160-170 of NANOLUC™ luciferase (C-$nano_{160-170}$).

TABLE 2

| Polypeptide Description | Sequence | SEQ ID NO: |
|---|---|---|
| NANOLUC ™ Luciferase | MVFTLEDFVGDWEQTAAYNLDQVLEQGGVSSLLQNLAVSVTPIQRIVRSGENA LKIDIHVIIPYEGLSADQMAQIEEVFKVVYPVDDHHFKVILPYGTLVIDGVTP NMLNYFGRPYEGIAVFDGKKITVTGTLWNGNKIIDERLITPDGSMLFRVTINS VTGYRLFEEIL | 1 |
| N-nanol-159 | MVFTLEDFVGDWEQTAAYNLDQVLEQGGVSSLLQNLAVSVTPIQRIVRSGENA LKIDIHVIIPYEGLSADQMAQIEEVFKVVYPVDDHHFKVILPYGTLVIDGVTP NMLNYFGRPYEGIAVFDGKKITVTGTLWNGNKIIDERLITPDGSMLFRVTINS | 2 |
| C-$nano_{160-170}$ | VTGYRLFEEIL | 3 |
| 141-206 of SNAP25b (human and rat) | ARENEMDENLEQVSGIIGNLRHMALDMGNEIDTQNRQIDRIMEKADSNKTRID EANQRATKMLGSG | 10 |
| 529-566 of human SV2C | NTYFKNCTFIDTVFDNTDFEPYKFIDSEFKNCSFFHNK | 11 |
| Firefly luciferase | MEDAKNIKKGPAPFYPLEDGTAGEQLHKAMKRYALVPGTIAFTDAHIEVDITY AEYFEMSVRLAEAMKRYGLNTNHRIVVCSENSLQFFMPVLGALFIGVAVAPAN DIYNERELLNSMGISQPTVVFVSKKGLQKILNVQKKLPIIQKIIIMDSKTDYQ GFQSMYTFVTSHLPPPGFNEYDFVPESFDRDKTIALIMNSSGSTGLPKGVALP HRTACVRFSHARDPIFGNQIIPDTAILSVVPFHHGFGMFTTLGYLICGFRVVL MYRFEEELFLRSLQDYKIQSALLVPTLFSFFAKSTLIDKYDLSNLHEIASGGA PLSKEVGEAVAKRFHLPGIRQGYGLTETTSAILITPEGDDKPGAVGKVVPFFE AKVVDLDTGKTLGVNQRGELCVRGPMIMSGYVNNPEATNALIDKDGWLHSGDI AYWDEDEHFFIVDRLKSLIKYKGYQVAPAELESILLQHPNIFDAGVAGLPDDD AGELPAAVVVLEHGKTMTEKEIVDYVASQVTTAKKLRGGVVFVDEVPKGLTGK LDARKIREILIKAKKGGKIAV | 13 |
| Human SNAP25b (NCBI Reference Sequence: NP_570824.1) | MAEDADMRNELEEMQRRADQLADESLESTRRMLQLVEESKDAGIRTLVMLDEQ GEQLERIEEGMDQINKDMKEAEKNLTDLGKFCGLCVCPCNKLKSSDAYKKAWG NNQDGVVASQPARVVDEREQMAISGGFIRRVTNDARENEMDENLEQVSGIIGN LRHMALDGMNEIDTQNRQIDRIMEKADSNKTRIDEANQRATKMLGSG | 14 |

TABLE 2-continued

| Polypeptide Description | Sequence | SEQ ID NO: |
|---|---|---|
| Sensor 1 DNA sequence | ATGGTCTTCACACTCGAAGATTTCGTTGGGGACTGGGAACAGACAGCCGCCTA CAACCTGGACCAAGTCCTTGAACAGGGAGGTGTGTCCAGTTTGCTGCAGAATC TCGCCGTGTCCGTAACTCCGATCCAAAGGATTGTCCGGAGCGGTGAAATGCC CTGAAGATCGACATCCATGTCATCATCCCGTATGAAGGTCTGAGCGCCGACCA AATGGCCCAGATCGAAGAGGTGTTTAAGGTGGTGTACCCTGTGGATGATCATC ACTTTAAGGTGATCCTGCCCTATGGCACACTGGTAATCGACGGGGTTACGCCG AACATGCTGAACTATTTCGGACGGCCGTATGAAGGCATCGCCGTGTTCGACGG CAAAAAGATCACTGTAACAGGGACCCTGTGGAACGGCAACAAAATTATCGACG AGCGCCTGATCACCCCCGACGGCTCCATGCTGTTCCGAGTAACCATCAACAGt gggagttccGGTGGTGGCGGGAGCGGAGGTGGAGGctcgAGCGGTgGAGCTCa gAACACCTACTTCAAGAACTGCACATTTATTGACACTGTTTTTGACAACACAG ATTTTGAGCCATATAAATTCATTGACAGTGAATTTAAAAACTGCTCGTTTTTT CACAACAAGGGGGGCGGAGGTTCCGCCCGGGAAAATGAAATGGATGAAAACCT AGAGCAGGTGAGCGGCATCATCGGAAACCTCCGTCATATGGCCCTAGACATGG GCAATGAGATTGACACCCAGAATCGCCAGATTGACAGGATCATGGAGAAGGCT GACTCCAACAAAACCAGAATTGATGAAGCCAACCAACGTGCAACAAAGATGCT GGGAAGTGGTggGAATTCtggcTCGAGcGGTGGTGGCGGGAGCGGAGGTGGAG GGtcgtcaGGTGTGACCGGCTACCGGCTGTTCGAGGAGATTCTGGCGGCCGCA CTCGAGCACCACCACCACCACCACTGA | 15 |
| Human VAMP1 | MSAPAQPPAE GTEGTAPGGG PPGPPPNMTS NRRLQQTQAQ VEEVVDIIRV NVDKVLERDQ KLSELDDRAD ALQAGASQFE SSAAKLKRKY WWKNCKMMIM LGAICAIIVV VIVIYFFT | 16 |
| Amino acids 32-52 of SYT1 | GEGKEDAFSKLKQKFMNELEIK | 17 |
| Amino acids 40-60 of SYT2 | GESQEDMFAKLKEKFFNEINK | 18 |
| Amino acids 60-87 of human VAMP2 | LSELDDRADAL QAGASQFETS AAKLKRK | 19 |
| Amino acids 43-70 of human VAMP3 | LSELDDRA DALQAGASQFETSAAKLKRK | 20 |
| Amino acids 62-89 of human VAMP 1 | LSELDDRAD ALQAGASQFE SSAAKLKRK | 21 |
| Sensor 2 DNA sequences | ATGGTCTTCACACTCGAAGATTTCGTTGGGGACTGGGAACAGACAGCCGCCTA CAACCTGGACCAAGTCCTTGAACAGGGAGGTGTGTCCAGTTTGCTGCAGAATC TCGCCGTGTCCGTAACTCCGATCCAAAGGATTGTCCGGAGCGGTGAAATGCC CTGAAGATCGACATCCATGTCATCATCCCGTATGAAGGTCTGAGCGCCGACCA AATGGCCCAGATCGAAGAGGTGTTTAAGGTGGTGTACCCTGTGGATGATCATC ACTTTAAGGTGATCCTGCCCTATGGCACACTGGTAATCGACGGGGTTACGCCG AACATGCTGAACTATTTCGGACGGCCGTATGAAGGCATCGCCGTGTTCGACGG CAAAAAGATCACTGTAACAGGGACCCTGTGGAACGGCAACAAAATTATCGACG AGCGCCTGATCACCCCCGACGGCTCCATGCTGTTCCGAGTAACCATCAACAGt gggagttccGGTGGTGGCGGGAGCGGAGGTGGAGGctcgAGCGGTgGAGCTCa gGCCCGGGAAAATGAAATGGATGAAAACCTAGAGCAGGTGAGCGGCATCATCG GAAACCTCCGTCATATGGCCCTAGACATGGGCAATGAGATTGACACCCAGAAT CGCCAGATTGACAGGATCATGGAGAAGGCTGACTCCAACAAAACCAGAATTGA TGAAGCCAACCAACGTGCAACAAAGATGCTGGGAAGTGGTggGAATTCtggcT CGAGcGGTGGTGGCGGGAGCGGAGGTGGAGGGtcgtcaGGTGTGACCGGCTAC CGGCTGTTCGAGGAGATTCTGGCGGCCGCACTCGAGCACCACCACCACCACCA CTGA | 29 |
| Sensor 3 DNA sequences | ATGGTCTTCACACTCGAAGATTTCGTTGGGGACTGGGAACAGACAGCCGCCTA CAACCTGGACCAAGTCCTTGAACAGGGAGGTGTGTCCAGTTTGCTGCAGAATC TCGCCGTGTCCGTAACTCCGATCCAAAGGATTGTCCGGAGCGGTGAAATGCC CTGAAGATCGACATCCATGTCATCATCCCGTATGAAGGTCTGAGCGCCGACCA AATGGCCCAGATCGAAGAGGTGTTTAAGGTGGTGTACCCTGTGGATGATCATC ACTTTAAGGTGATCCTGCCCTATGGCACACTGGTAATCGACGGGGTTACGCCG AACATGCTGAACTATTTCGGACGGCCGTATGAAGGCATCGCCGTGTTCGACGG CAAAAAGATCACTGTAACAGGGACCCTGTGGAACGGCAACAAAATTATCGACG AGCGCCTGATCACCCCCGACGGCTCCATGCTGTTCCGAGTAACCATCAACAGt gggagttccGGTGGTGGCGGGAGCGGAGGTGGAGGctcgAGCGGTgGAGCTCa gCAGCAAACCCAGGCACAAGTGGAGGAGGTGGTGGACATCATACGTGTGAACG TGGACAAGGTCCTGGAGAGGGACCAGAAGCTGTCAGAGCTGGATGACCGAGCT | 30 |

TABLE 2-continued

| Polypeptide Description | Sequence | SEQ ID NO: |
|---|---|---|
| | GATGCCTTGCAGGCAGGAGCATCACAATTTGAGAGCAGTGCTGCCAAGCTAAA<br>GAGGAAGTATTGGTGGAAAAACTGCAAGggGAATTCtggcTCGAGcGGTGGTG<br>GCGGGAGCGGAGGTGGAGGGtcgtcaGGTGTGACCGGCTACCGGCTGTTCGAG<br>GAGATTCTGGCGGCCGCACTCGAGCACCACCACCACCACCACTGA | |
| In vivo construct DNA sequences | ATGGTCTTCACACTCGAAGATTTCGTTGGGGACTGGGAACAGACAGCCGCCTA<br>CAACCTGGACCAAGTCCTTGAACAGGGAGGTGTGTCCAGTTTGCTGCAGAATC<br>TCGCCGTGTCCGTAACTCCGATCCAAAGGATTGTCCGGAGCGGTGAAAATGCC<br>CTGAAGATCGACATCCATGTCATCATCCCGTATGAAGGTCTGAGCGCCGACCA<br>AATGGCCCAGATCGAAGAGGTGTTTAAGGTGGTGTACCCTGTGGATGATCAT<br>ACTTTAAGGTGATCCTGCCCTATGGCACACTGGTAATCGACGGGGTTACGCCG<br>AACATGCTGAACTATTTCGGACGGCCGTATGAAGGCATCGCCGTGTTCGACGG<br>CAAAAAGATCACTGTAACAGGGACCCTGTGGAACGGCAACAAAATTATCGACG<br>AGCGCCTGATCACCCCCGACGGCTCCATGCTGTTCCGAGTAACCATCAACAGt<br>gggagttccGGTGGTGGCGGGAGCGGAGGTGGAGGctcgAGCGGTgGAGCTCa<br>gGAAGATGCCAAAAACATTAAGAAGGGCCCAGCGCCATTCTACCCACTCGAAG<br>ACGGGACCGCCGGCGAGCAGCTGCACAAAGCCATGAAGCGCTACGCCCTGGTG<br>CCCGGCACCATCGCCTTTACCGACGCACATATCGAGGTGGACATTACCTACGC<br>CGAGTACTTCGAGATGAGCGTTCGGCTGGCAGAAGCTATGAAGCGCTATGGGC<br>TGAATACAAACCATCGGATCGTGGTGTGCAGCGAGAATAGCTTGCAGTTCTTC<br>ATGCCCGTGTTGGGTGCCCTGTTCATCGGTGTGGCTGTGGCCCCAGCTAACGA<br>CATCTACAACGAGCGCGAGCTGCTGAACAGCATGGGCATCAGCCAGCCCACCG<br>TCGTATTCGTGAGCAAGAAAGGGCTGCAAAAGATCCTCAACGTGCAAAAGAAG<br>CTACCGATCATACAAAAGATCATCATCATGGATAGCAAGACCGACTACCAGGG<br>CTTCCAAAGCATGTACACCTTCGTGACTTCCCATTTGCCACCCGGCTTCAACG<br>AGTACGACTTCGTGCCCGAGAGCTTCGACCGGGACAAAACCATCGCCCTGATC<br>ATGAACAGTAGTGGCAGTACCGGATTGCCCAAGGGCGTAGCCCTACCGCACCG<br>CACCGCTTGTGTCCGATTCAGTCATGCCCGCGACCCCATCTTCGGCAACCAGA<br>TCATCCCCGACACCGCTATCCTCAGCGTGGTGCCATTTCACCACGGCTTCGGC<br>ATGTTCACCACGCTGGGCTACTTGATCTGCGGCTTTCGGGTCGTGCTCATGTA<br>CCGCTTCGAGGAGGAGCTATTCTTGCGCAGCTTGCAAGACTATAAGATTCAAT<br>CTGCCCTGCTGGTGCCCACACTATTTAGCTTCTTCGCTAAGAGCACTCTCATC<br>GACAAGTACGACCTAAGCAACTTGCACGAGATCGCCAGCGGCGGGGCGCCGCT<br>CAGCAAGGAGGTAGGTGAGGCCGTGGCCAAACGCTTCCACCTACCAGGCATCC<br>GCCAGGGCTACGGCCTGACAGAAACAACCAGCGCCATTCTGATCACCCCCGAA<br>GGGGACGACAAGCCTGGCGCAGTAGGCAAGGTGGTGCCCTTCTTCGAGGCTAA<br>GGTGGTGGACTTGGACACCGGTAAGACACTGGGTGTGAACCAGCGCGGCGAGC<br>TGTGCGTCCGTGGCCCCATGATCATGAGCGGCTACGTTAACAACCCCGAGGCT<br>ACAAACGCTCTCATCGACAAGGACGGCTGGCTGCACAGCGGCGACATCGCCTA<br>CTGGGACGAGGACGAGCACTTCTTCATCGTGGACCGGCTGAAGAGCCTGATCA<br>AATACAAGGGCTACCAGGTAGCCCCAGCCGAACTGGAGAGCATCCTGCTGCAA<br>CACCCCAACATCTTCGACGCCGGGGTCGCCGGCCTGCCCGACGACGATGCCGG<br>CGAGCTGCCCGCCGCAGTCGTCGTGCTGGAACACGGTAAAACCATGACCGAGA<br>AGGAGATCGTGGACTATGTGGCCAGCCAGGTTACAACCGCCAAGAAGCTGCGC<br>GGTGGTGTTGTGTTCGTGGACGAGGTGCCTAAAGGACTGACCGGCAAGTTGGA<br>CGCCCGCAAGATCCGCGAGATTCTCATTAAGGCCAAGAAGGGCGGCAAGATCG<br>CCGTGGGGGCGGAGGTTCCGCCGAGGACGCAGACATGCGTAATGAACTGGAG<br>GAGATGCAGAGGAGGGCTGACCAGCTGGCTGATGAGTCCCTGGAAAGCACCCG<br>TCGCATGCTGCAGCTGGTCGAAGAGAGTAAAGATGCTGGCATCAGGACTTTGG<br>TTATGTTGGATGAGCAAGGCGAACAACTGGAACGCATTGAGGAAGGGATGGAC<br>CAAATCAATAAGGATATGAAAGAAGCAGAAAAGAATTTGACGGACCTAGGAAA<br>ATTCTGCGGGCTTTGTGTGTGTCCCTGTAACAAGCTTAAATCCAGTGATGCTT<br>ACAAAAAAGCCTGGGGCAATAATCAGGATGGAGTAGTGGCCAGCCAGCCTGCC<br>CGTGTGGTGGATGAACGGGAGCAGATGGCCATCAGTGGTGGCTTCATCCGCAG<br>GGTAACAAACGATGCCCGGGAAAATGAAATGGATGAAAACCTAGAGCAGGTGA<br>GCGGCATCATCGGAAACCTCCGTCATATGGCCCTAGACATGGGCAATGAGATT<br>GACACCCAGAATCGCCAGATTGACAGGATCATGGAGAAGGCTGACTCCAACAA<br>AACCAGAATTGATGAAGCCAACCAACGTGCAACAAAGATGCTGGGAAGTGGTg<br>gGAATTCtggcTCGAGcGGTGGTGGCGGGAGCGGAGGTGGAGGGtcgtcaGGT<br>GTGACCGGCTACCGGCTGTTCGAGGAGATTCTGTAA | 31 |

In one aspect of any of the embodiments, described herein is a nucleic acid comprising a nucleotide sequence that encodes a single chain polypeptide as described herein. In some embodiments of any of the aspects described herein, the nucleic acid can comprise SEQ ID NO: 15, 29, 30, or 31.

Another aspect of the invention relates to a nucleic acid vector comprising the nucleic acid molecule described herein. In one embodiment the vector is an expression vector. Such an expression vector is referred to herein as an expression construct, and comprises a nucleic acid molecule disclosed herein operably-linked to the expression vector useful for expressing the nucleic acid molecule in a cell or cell-free extract. A wide variety of expression vectors can be employed for expressing a nucleic acid molecule encoding a single chain polypeptide of the present invention including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express the single chain polypeptide under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

In one aspect of any of the embodiments, described herein is a nucleic acid vector comprising a nucleic acid comprising a nucleotide sequence that encodes a single chain polypeptide as described herein. In some embodiments of any of the aspects described herein, the nucleic acid can comprise SEQ ID NO: 15. In some embodiments of any of the aspects described herein, the vector can be an expression vector and comprise the nucleic acid sequence in expressible form. In some embodiments of any of the aspects described herein, the vector can be a viral expression vector, a prokaryotic expression vector, a yeast expression vector, an insect expression vector, or a mammalian expression vector.

The term "vector", as used herein, refers to a nucleic acid construct designed for delivery to a cell or transfer between different cells. Many vectors useful for transferring exogenous genes into target cells are available, e.g. the vectors may be episomal, e.g., plasmids, virus derived vectors or may be integrated into the target cell genome, through homologous recombination or random integration. In some embodiments of any of the aspects described herein, a vector can be an expression vector. As used herein, the term "expression vector" refers to a vector that has the ability to incorporate and express heterologous nucleic acid fragments in a cell. An expression vector may comprise additional elements. The nucleic acid incorporated into the vector can be operatively linked to an expression control sequence when the expression control sequence controls and regulates the transcription and translation of that polynucleotide sequence.

Another aspect of the invention relates to a cell comprising the nucleic acid molecule or expression construct described herein. The cell can be for propagation of the nucleic acid or for expression of the nucleic acid, or both. In one aspect of any of the embodiments, described herein is a cell comprising a nucleic acid and/or vector as described herein. In some embodiments of any of the aspects described herein, the cell expresses a single chain polypeptide as described herein. In some embodiments of any of the aspects described herein, the cell can be a prokaryotic cell, an *E. coli* cell, a yeast cell, an insect cell, an animal cell, a mammalian cell, a human cell, a mouse cell, a primate cell, and/or a neuronal cell. In some embodiments of any of the aspects, the cell is a neuronal cell, in particular, cells with a high sensitivity to BoNT.

A cell with a high sensitivity to BoNT is a cell which is susceptible to BoNT intoxication. In some embodiments, a cell with a high sensitivity to BoNT is a cell which is susceptible to BoNT intoxication by, e.g., about 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less A, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM, about 0.1 pM or less of a BoNT, about 90 fM or less of a BoNT, about 80 fM or less of a BoNT, about 70 fM or less of a BoNT, about 60 fM or less of a BoNT, about 50 fM or less of a BoNT, about 40 fM or less of a BoNT, about 30 fM or less of a BoNT, about 20 fM or less of a BoNT, or about 10 fM or less of a BoNT.

In some embodiments, the cell is a primary neuronal cell with a high sensitivity to BoNT, e.g., cortical neurons, hippocampal neurons, and/or spinal cord neurons.

In some embodiments, the cell is from a neuronal cell line with a high sensitivity to BoNT, e.g. BE(2)-M17, Kelly, LA1-55n, N1 E-115, N4TG3, N18, Neuro-2a, NG108-15, PC12, SH-SY5Y, SiMa, and/or SK-N-BE(2)-C.

In some embodiments, the cell is a neuronal cell derived from a stem cell, in particular from an induced pluripotent stem cell (iPS cell), eg. i-Cell® Neurons, i-Cell® DopaNeurons iCell Glutamatergic Neurons, iCell MotoNeurons (Cellular dynamics Inc) Cerebral Cortical Neurons, Neural Stem Cells (Axol Biosciences), Peri.4U neurons, CNS.4U neurons, Dopa.4UNeurons (Axiogenesis) MNP cells (Lonza), Cortical Neurons, Motor Neurons (iStem), and/or iPSC-Derived Neural Cells (MTI-GlobalStem).

In some embodiments of any of the aspects, the cell can be a prokaryotic cell, including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridium perfringens, Clostridium difficile, Caulobacter crescentus, Lactococcus lactis, Methylobacterium extorquens, Neisseria meningirulls, Neisseria meningitidis, Pseudomonas fluorescens* and *Salmonella typhimurium*; and a eukaryotic cell including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; a insect cell or cell line derived from insects, such as, e.g., those derived from *Spodoptera frugiperda, Trichoplusia ni, Drosophila melanogaster* and *Manduca sexta*; or a mammalian cell or cell line derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4.sup.th ed. 2000); ANIMAL CELL CULTURE: A PRACTICAL APPROACH (John R. W. Masters ed., Oxford University Press, 3.sup.rd ed. 2000); MOLECULAR CLONING A LABORATORY MANUAL, supra, (2001); BASIC CELL CULTURE: A PRACTICAL APPROACH (John M. Davis, Oxford Press, 2.sup.nd ed. 2002); and CURRENT PROTOCOLS IN MOLECULAR BIOLOGY, supra, (2004). These protocols are routine procedures within the scope of one skilled in the art and from the teaching herein.

The compositions described herein can be used in methods to detect and/or measure the presence, potency, and/or activity of, e.g., a neurotoxin (e.g. BoNT). In the presence of any BoNT, a single chain polypeptide with a BoNT cleavage site will be cleaved in the linker sequence, disrupting the activity of the split reporter protein (e.g. luciferase). Accordingly, a decrease in the activity of the reporter protein indicates the presence of BoNT. In one aspect of any of the embodiments, described herein is a method for detecting *C. botulinum* neurotoxin (BoNT) activity in a sample, comprising: a) contacting the sample to a single chain polypeptide as described herein, under conditions appropriate for BoNT activity; and determining luciferase activity of the polypeptide, as compared to luciferase activity of the polypeptide in the absence of the sample, wherein a decrease of luciferase activity indicates BoNT activity in the sample. In one aspect of any of the embodiments, described herein is a method for determining the potency of a botulinum neurotoxin, comprising: a) contacting the neurotoxin to a single chain polypeptide as described herein under conditions appropriate for BoNT activity; and b) determining the luciferase activity of the polypeptide, as compared to a reference, thereby determining the potency. In some embodiments of any of the aspects, the methods are suitable for batch release, e.g. for batch release testing and/or lot release testing. In some embodiments of any of the aspects described herein, the methods described herein can be performed in vitro.

In one aspect of any of the embodiments, described herein is a method for detecting *C. botulinum* neurotoxin (BoNT) activity in a sample, comprising: a) contacting the sample to a single chain polypeptide as described herein, under conditions appropriate for BoNT activity; and b) determining luciferase activity of the polypeptide, as compared to luciferase activity of the polypeptide in the absence of the sample, wherein a decrease of luciferase activity indicates BoNT activity in the sample. In one aspect of any of the embodiments, described herein is a method for detecting *C. botulinum* neurotoxin (BoNT) activity in a sample, comprising: a) contacting the sample to a single chain polypeptide comprising: amino acids 1-159 of NANOLUC™ luciferase (N-nano$_{1-159}$), amino acids 160-170 of NANOLUC™ luciferase (C-nano$_{160-170}$), separated and functionally joined by a linker comprising a BoNT cleavage site located C-terminal to the N-nano$_{1-159}$; and N-terminal to the C-nano$_{160-170}$, under conditions appropriate for BoNT activity; and b) determining luciferase activity of the polypeptide, as compared to luciferase activity of the polypeptide in the absence of the sample, wherein a decrease of luciferase activity indicates BoNT activity in the sample.

In one aspect of any of the embodiments, described herein is a method for detecting *C. botulinum* neurotoxin (BoNT) activity in a sample, comprising: a) contacting the sample to a single chain polypeptide comprising: amino acids 1-159 of NANOLUC™ luciferase (N-nano$_{1-159}$), amino acids 160-170 of NANOLUC™ luciferase (C-nano$_{160-170}$), separated and functionally joined by a linker comprising a BoNT cleavage site located C-terminal to the N-nano$_{1-159}$; and N-terminal to the C-nano$_{160-170}$, under conditions appropriate for BoNT activity; and b) determining luciferase activity of the polypeptide, as compared to activity of the polypeptide in the absence of the sample, wherein a decrease in the luciferase activity is an indication of BoNT activity in the sample. In some embodiments of any the aspects described herein, the linker comprises a first spacer of 5 to 15 amino acids, a binding fragment of amino acids 529-566 of human SV2C located C-terminal to the first spacer and N-terminal to the BoNT cleavage site, and a second spacer of 5 to 15 amino acids located C-terminal to the BoNT cleavage site, wherein the BoNT cleavage site comprises amino acids 141-206 of human SNAP25. In some embodiments of any the aspects described herein, the linker comprises a first spacer of 5 to 15 amino acids located N-terminal to the BoNT cleavage site, and a second spacer of 5 to 15 amino acids located C-terminal to the BoNT cleavage site, wherein the BoNT cleavage site comprises amino acids 141-206 of human SNAP25. In some embodiments of any the aspects described herein, the linker comprises a first spacer of 5 to 15 amino acids located N-terminal to the BoNT cleavage site, a second spacer of 5 to 15 amino acids located C-terminal to the BoNT cleavage site, wherein the BoNT cleavage site comprises amino acids 35-96 of human VAMP1.

In one aspect of any of the embodiments, described herein is a method for determining the EC50 of a BoNT, comprising: a) contacting a single chain polypeptide as described herein, under conditions appropriate for BoNT activity with the BoNT at a first concentration; and determining luciferase activity of the polypeptide, as compared to luciferase activity of the polypeptide in the absence of the sample; b) repeating step a) at a different concentration of the BoNT until the EC50 can be determined. In some embodiments of any of the aspects described herein, the different concentrations of BoNT encompass at least one order of magnitude difference.

As known in the art, the "half maximal effective concentration (EC50)" refers to the concentration of a drug, antibody or toxicant which induces a response halfway between the baseline and maximum after some specified exposure time. It is commonly used as a measure of drug's potency. The EC50 of a graded dose response curve therefore represents the concentration of a compound where 50% of its maximal effect is observed. The EC50 of a quantal dose response curve represents the concentration of a compound where 50% of the population exhibits a response, after a specific exposure duration.

As used herein, "conditions appropriate for BoNT activity" refers to conditions (e.g. temperature, pH, cofactors, etc) under which BoNT can specifically cleave a BoNT cleavage site. In some embodiments of any of the aspects described herein, conditions appropriate for BoNT activity can comprise a buffer of HEPES, 20 µM $ZnCl_2$, 2 mM DTT, 1 mg/ml BSA, pH 7.1. In some embodiments of any of the aspects described herein, conditions appropriate for BoNT activity can comprise a buffer of HEPES, 10-30 µM $ZnCl_2$, 1-3 mM DTT, 0.5-2 mg/ml BSA, pH 6.5-7.5. In some embodiments of any of the aspects described herein, conditions appropriate for BoNT activity can comprise a buffer of HEPES, 5-50 µM $ZnCl_2$, 0.1-10 mM DTT, 0.1-10 mg/ml BSA, pH 6.5-7.5.

In some embodiments of any of the aspects described herein, the conditions can comprise incubation at about 37° C. for a period of from about 1 hour to about 36 hours. In some embodiments of any of the aspects described herein, the conditions can comprise incubation at about 37° C. for a period of from 1 hour to 36 hours. In some embodiments of any of the aspects described herein, the conditions can comprise incubation at about 37° C. for a period of from about 1 hour to about 24 hours. In some embodiments of any of the aspects described herein, the conditions can comprise incubation at about 37° C. for a period of from 1 hour to 24 hours. In some embodiments of any of the aspects described herein, the conditions can comprise incubation at about 37° C. for a period of from about 4 hours to about 24 hours. In some embodiments of any of the aspects described herein, the conditions can comprise incubation at about 37° C. for a period of from 4 hours to 24 hours.

In some embodiments of any of the aspects described herein, the single chain polypeptide is present at a concentration of from about 3 nM to about 300 nM. In some embodiments of any of the aspects described herein, the single chain polypeptide is present at a concentration of from 3 nM to 300 nM. In some embodiments of any of the aspects described herein, the single chain polypeptide is present at a concentration of from about 30 nM to about 300 nM. In some embodiments of any of the aspects described herein, the single chain polypeptide is present at a concentration of from 30 nM to 300 nM. In some embodiments of any of the aspects described herein, the single chain polypeptide is present at a concentration of about 30 nM. In some embodiments of any of the aspects described herein, the single chain polypeptide is present at a concentration of 30 nM.

BoNT activity can also be detected in cells, e.g., in neuronal cells. In one aspect of any of the embodiments, described herein is a method for detecting C. botulinum neurotoxin (BoNT) activity in a sample, comprising: a) contacting the sample to neuronal cells expressing a single chain polypeptide as described herein; b) incubating the neuronal cells for a period of from about 12 hours to about 60 hours; c) harvesting lysate from the neuronal cells; and d) measuring NANOLUC™ luciferase activity in the lysate, as compared to NANOLUC™ luciferase activity in identically treated neuronal cells in the absence of the sample, wherein a decrease in the NANOLUC™ luciferase activity indicates BoNT activity in the sample. In one aspect of any of the embodiments, described herein is a method for detecting C. botulinum neurotoxin (BoNT) activity in a sample, comprising: a) contacting the sample to neuronal cells expressing a single chain polypeptide comprising: amino acids 1-159 of NANOLUC™ luciferase (N-nano$_{1-159}$), amino acids 160-170 of NANOLUC™ luciferase (C-nano$_{160-170}$), separated and functionally joined by a linker comprising a BoNT cleavage site located C-terminal to the N-nano$_{1-159}$ and N-terminal to the C-nano$_{160-170}$; b) incubating the neuronal cells for a period of from about 12 hours to about 60 hours; c) harvesting lysate from the neuronal cells; and d) measuring NANOLUC™ luciferase activity in the lysate, as compared to NANOLUC™ luciferase activity in identically treated neuronal cells in the absence of the sample, wherein a decrease in the NANOLUC™ luciferase activity indicates BoNT activity in the sample. In some embodiments of any of the aspects described herein, the linker further comprises an intact second luciferase polypeptide located between the N-nano$_{1-159}$ and the cleavage site. In some embodiments of any of the aspects described herein, the neuronal cells express the single chain polypeptide from a viral expression vector. In some embodiments of any of the aspects described herein, the neuronal cells express the single chain polypeptide from a viral expression vector for at least 3 days prior to the contacting step. In some embodiments of any of the aspects described herein, the neuronal cells express the single chain polypeptide from a viral expression vector for at least 4 days prior to the contacting step. In some embodiments of any of the aspects described herein, the neuronal cells express the single chain polypeptide from a viral expression vector for at least 6 days prior to the contacting step. In some embodiments of any of the aspects described herein, the neuronal cells express the single chain polypeptide from a viral expression vector for 6 days prior to the contacting step. In some embodiments of any of the aspects described herein, the viral expression system is a lentivirus expression system. In some embodiments of any of the aspects described herein, the incubating step b) is from about 12 hours to about 72 hours. In some embodiments of any of the aspects described herein, the incubating step b) is about 48 hours. In some embodiments of any of the aspects described herein, the incubating step b) is 48 hours.

In some embodiments of any of the aspects described herein, the step of harvesting lysate can comprise addition of a lysis buffer. In some embodiments of any of the aspects described herein, the step of harvesting lysate can comprise centrifugation and/or sedimentation.

In some embodiments of any of the aspects described herein, a method can comprise the use of a combination of single chain polypeptides, each polypeptide having a different BoNT cleavage sites and/or combination of BoNT cleavage sites.

As used herein, "determining luciferase activity" refers to detecting, quantitatively or qualitatively, the level of light being generated by a luciferase (or a sample that may contain functional luciferase) in the presence of a luciferase substrate. Luminesence can be detected by any means known in the art, e.g., by luminescence microscopy, photometers, luminescence plate readers, photomultiplier detectors, and the like.

Luciferase substrates can include naturally-occurring luciferins as well as engineered substrates. Luciferins, for example, include firefly luciferin, Cypridina [also known as Vargula] luciferin [coelenterazine], bacterial luciferin, as well as synthetic analogs of these substrates. In some embodiments of any of the aspects described herein, the luciferin is coelenterazine and analogues thereof, which include molecules in U.S. Pat. No. 6,436,682, which is incorporated herein in its entirety by reference, and for example, see Zhao et al, (2004), Mol Imaging, 3; 43-54. Additional substrates are described in, e.g., U.S. Pat. Nos. 5,374,534; 5,098,828; 6,436,682; 5,004,565; 5,455,357; and 4,950,588, each of which is incorporated herein in its entirety by reference.

In some embodiments of any of the aspects, the luciferase activity can be determined by addition of luciferase substrate to the single chain polypeptide and quantitative measurement of a luminescent signal produced. In some embodiments of any of the aspects described herein, the substrate for NANOLUC™ luciferase can be furimazine (2-furanyl-methyl-deoxy-coelenterazine).

In some embodiments of any of the aspects described herein, the method can further comprise measuring the activity of a second luciferase comprised by the single chain polypeptide. In some embodiments of any of the aspects described herein, the activity of the second luciferase can be measured in the cell lysate. In some embodiments of any of the aspects described herein, the activity of the second luciferase can permit normalization of expression of the single chain polypeptide across samples, cells, cell populations, and/or wells. In some embodiments of any of the aspects described herein, the luciferase activity of the second luciferase polypeptide in the sample is determined and used as an indicator of total single chain polypeptide present in the harvested lysate.

In one aspect of any of the embodiments, described herein is a kit comprising: a) one or more single chain polypeptides as described herein, with each or a combination of the single chain polypeptides packaged into a separate container; one or more nucleic acids or nucleic acid vectors as described herein, with each or a combination of the nucleic acids or nucleic acid vectors packaged into a separate container;

and/or one or more cells as described herein with each or a combination of the cells packaged into a separate container.

A kit is any manufacture (e.g., a package or container) comprising at least one reagent, e.g., a single chain polypeptide, nucleic acid encoding a single chain polypeptide, or cell comprising a nucleic acid encoding a single chain polypeptide as described herein, the manufacture being promoted, distributed, or sold as a unit for performing the methods or assays described herein.

The kits described herein include reagents and/or components that permit assaying the level of activity of a reporter, e.g., one or more types of luciferase. Such reagents comprise in addition to single chain polypeptides, for example, buffer solutions, substrates, or washing liquids etc. Furthermore, the kit can comprise an amount of a neurotoxin, e.g., BoNT, or luciferase which can be used for a calibration of the kit or as an internal control. Additionally, the kit may comprise an instruction leaflet and/or may provide information as to the relevance of the obtained results For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects described herein, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more.

The terms "increased", "increase", "enhance", or "activate" are all used herein to mean an increase by a statically significant amount. In some embodiments of any of the aspects described herein, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker, an "increase" is a statistically significant increase in such marker level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects described herein, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of botulinum activity. A subject can be male or female.

As used herein, the term "binding activity" means that one molecule is contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. "Bound" and "bind" are considered terms for binding.

In some embodiments of any of the aspects described herein, a single chain polypeptide can be isolated or purified. By "isolated" is meant a material that is free to varying degrees from components which normally accompany it as found in its native state. "Isolate" denotes a degree of separation from original source or surroundings, e.g. from a cell or cell lysate.

The term "purified" is used to refer to a substance such as a polypeptide that is "substantially pure", with respect to other components of a preparation (e.g., other polypeptides). It can refer to a polypeptide that is at least about 50%, 60%, 70%, or 75%, preferably at least about 85%, more preferably at least about 90%, and most preferably at least about 95% pure, with respect to other components. Recast, the terms "substantially pure" or "essentially purified", with regard to a polypeptide, refers to a preparation that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

As used herein, "contacting" refers to any suitable means for delivering, or exposing, a sample or agent to a single chain polypeptide as described herein (or a cell comprising said polypeptide). Exemplary delivery methods include, but are not limited to, direct delivery to a sample or to a cell culture medium, perfusion, injection, or other delivery method well known to one skilled in the art.

The term "sample" or "test sample" as used herein denotes a sample taken or isolated from any source, e.g., biological, environmental, industrial, or otherwise. The term also includes a mixture of the above-mentioned samples. The term "test sample" also includes untreated or pretreated (or pre-processed) samples. The test sample can be obtained by removing a sample from the source, but can also be accomplished by using a previously isolated sample (e.g. isolated at a prior timepoint and isolated by the same or another person).

In some embodiments of any of the aspects described herein, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects described herein, the test sample can be a frozen test sample, e.g., a frozen environmental sample, frozen industrial sample, or frozen tissue. The frozen sample can be thawed before employing methods, assays and systems described herein. After thawing, a frozen sample can be centrifuged before being subjected to methods, assays and systems described herein. In some embodiments of any of the aspects described herein, the test sample is a clarified test sample prepared, for example, by centrifugation and collection of a supernatant. In some embodiments of any of the aspects described herein, a test sample can be a pre-processed test sample, for example, supernatant or filtrate resulting from a treatment selected from the group consisting of centrifugation, filtration, thawing, purification, and any combinations thereof. In some embodiments of any of the aspects described herein, the test sample can be treated with a chemical and/or biological reagent. Chemical and/or biological reagents can be employed to protect and/or maintain the stability of the sample, including biomolecules (e.g., protein) therein, during processing. The skilled artisan is well aware of methods and processes appropriate for pre-processing of biological samples required for determination of the level of an expression product as described herein.

As used herein, the term "neuronal cell" or "neuron" refers to cells found in the nervous system that are specialized to receive, process, and transmit information as nerve signals. Neurons can include a central cell body or soma, and two types of projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the nervous system.

As used herein, the term "specific" refers to a particular interaction (e.g. binding and/or cleavage) between two molecules wherein a first entity interacts with a second, target entity with greater specificity and affinity than it interacts with a third entity which is a non-target. In some embodiments of any of the aspects described herein, specific can refer to an interaction of the first entity with the second target entity which is at least 10 times, at least 50 times, at least 100 times, at least 500 times, at least 1000 times or greater than the interaction with the third nontarget entity. A reagent specific for a given target is one that exhibits, e.g. specific binding for that target under the conditions of the assay being utilized or specific cleavage of a target sequence under the conditions of the assay being utilized.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. polypeptide binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects described herein, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects described herein, the polypeptide described herein can be a variant of a sequence described herein. In some embodiments of any of the aspects described herein, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, for example, genomic DNA or cDNA. Suitable RNA can include, for example, mRNA.

In some embodiments of any of the aspects described herein, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, In some embodiments of any of the aspects described herein, be combined with other suitable compositions and therapies. In some embodiments of any of the aspects described herein, the vector is episomal. The use of a suitable episomal vector provides a means of maintaining the nucleotide of interest in a subject or cell in high copy number extra chromosomal DNA thereby eliminating potential effects of chromosomal integration.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Example 1: Novel In Vitro and Cell-Based Assays for Measuring the Activity of Botulinum Neurotoxins Botulinum neurotoxins are a family of seven bacterial toxins (BoNT/A-G). They are one of the six Category A potential bioterrorism agents. These toxins have also been widely used to treat a growing list of medical conditions, with a market over two billion dollars. Detection and characterization of BoNTs have relied on the classic mouse lethal dose (LD50) assay. There is a pressing need, from both biodefense purposes and for medical product development to replace the animal assay with more convenient, sensitive, and accurate in vitro and cell-based assays.

Currently available in vitro assays for detecting and characterizing toxin activity have been developed, with various sensitivity. There are two major commercialized assays, both of which are based on fluorescence detection of the cleavage of the substrates by the enzymatic domain of toxins. The first of these assays is SNAPtide™ (List Biologics), involving the use of synthetic peptides containing the native cleavage site for BoNTs and labeled with two fluorescent dyes. The fluorescence signals are normally quenched between two dyes, and the signals rise once the peptide is cleaved by BoNTs. The second assay is BoTest™ (BioSentinel LLC). A cyan fluorescent protein (CFP) is linked through a peptide sequence to a yellow florescent protein (YFP). Cleavage of the linker by BoNTs abolishes the fluorescence resonance energy transfer (FRET) between CFP and YFP that can be detected.

Both assays provide sensitive and convenient ways to detect toxins and characterize toxin activities and are now widely used in laboratories. A significant drawback with these assays is that these fluorescent assays are prone to the interference from serum albumin proteins that present at high levels in the pharmaceutical products of toxins and clinical samples. A current solution is to purify toxins out of these samples with specific toxin antibodies prior to these fluorescence assays, but it adds significant cost to the assay and requires special agents (toxin antibodies) that are not readily available.

Numerous mice are currently utilized every year to quantify the toxin activity by pharmaceutical companies. There is a pressing need to develop a cell based assay to replace the mouse bio-assay, in order to reduce the use of animals in production of BoNTs. Cell based assays offer the ability to examine all aspects of toxin activity, including receptor binding, membrane translocation, and enzymatic activities. These aspects are not captured by any in vitro assays. Currently, there is only one cell based assay that is well established by a major pharmaceutical company (Allergan). This assay is an ELISA-type assay based on using a monoclonal antibody that recognizes the SNAP-25 protein cleaved by BoNT/A. Briefly, cells are exposed to BoNT/A and cleaved SNAP-25 is pulled down and immobilized by a special antibody that only recognizes the cleaved SNAP-25, but not the full length protein. Immobilized SNAP-25 is then detected by a second SNAP-25 antibody. This assay offers good sensitivity and can potentially replace the mouse assay. It is approved by the FDA for quantifying toxin products. The major drawback is that it relies on a specialized antibody generated by Allergan.

Alternative assays that are under development include using CFP-SNAP-25-YFP as substrates in cells (BioSentinel LLC). Cleavage of this fusion protein in cells abolishes the FRET signals between CFP and YFP. The major drawback is that this assay also requires complicated equipment such as a florescence microscope.

Described herein is a new assay developed to detect and measure the activity of BoNTs in vitro and in vivo. The assay is based on the development of a split form of luciferase. NANOLUC™ luciferase is a new generation of luciferase with superb protein stability and greatly increased luminescent signals (>100-fold higher than the classic firefly luciferase). This luciferase can be split into two pieces. When these two pieces are close to each other, they can reconstitute into a full active form that generates luminescent signals. Luminescent signals are abolished when these two pieces are separated from each other. In an illustrative embodiment depicted in FIG. 1, a linker region derived from the toxin substrates (SNAP-25 for BoNT/A, E, and C, synaptobrevin for BoNT/B, D, F, G) is inserted between two fragments of NANOLUC™ luciferase. Cleavage of this linker region by BoNTs separates the two fragments of NANOLUC™ luciferase and abolishes its activity, resulting in a reduction in luminescent signals. To demonstrate the feasibility of this approach, the following toxin sensors were designed and tested.

In vitro toxin sensors: Three different in vitro prototype toxin sensors were created and tested (FIG. 2A-FIG. 2B, FIG. 3A-FIG. 3B). The first sensor contains a SNAP-25 fragment that can be cleaved by BoNT/A, E, and C between the two split NANOLUC™ fragments (N-nano and C-nano, respectively, FIG. 2A-FIG. 2B). The second sensor contains an additional fragment of SV2C that serves as a toxin receptor, which can increase the cleavage efficiency by enhancing the interactions between toxins and sensor. The third version contains a synaptobrevin fragment that can be cleaved by BoNT/B, D, F, and G (FIG. 3A-FIG. 3B).

Figures 2A, 2B:
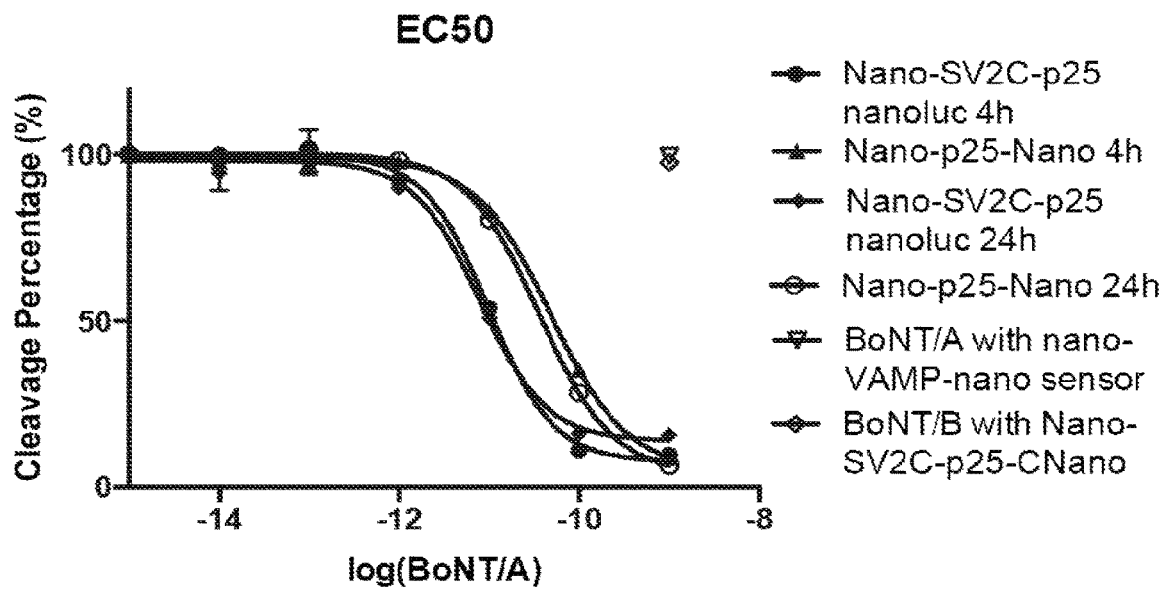
FIG. 2A-FIG. 2B demonstrate an in vitro detection assay of BoNT/A. Two sensor proteins were designed and investigated for BoNT/A toxin detection. One is $N_{Nano}$-SV2C-L4-p25-$C_{Nano}$ whereas the other one is $N_{Nano}$-p25-$C_{Nano}$. They were prepared at 30 nM in 30 ul volume while the BoNT/A was diluted from 1 nM to 1 fM with factor 10. The negative control was BoNT/B added in the sensor protein solution. The curve (FIG. 2A) was plotted based on the percentage of luminescence of NANOLUC™ luciferase. EC50 of using $N_{Nano}$-SV2C-p25-$C_{Nano}$ for BoNT/A is 9.73 pM after 4 h and 7.86 pM after 24 h, meanwhile EC50 of using $N_{Nano}$-p25-$C_{Nano}$ is 48.26 pM after 4 h and 35.87 pM after 24 h at 37° C. The sensor protein containing SV2C-L4 which is BoNT/A binding domain showed approximate 5-fold increase of EC50 (FIG. 2B).

These sensor proteins were purified as recombinant proteins. The two versions of sensors containing SNAP-25 were incubated with a gradient of concentrations of BoNT/A for either 4 or 24 hours. The remaining luciferase activities were measured and plotted as shown in FIG. 2A. As a control, it was found that BoNT/B did not affect the luciferase activity of these two sensors, demonstrating the specificity of these two sensors for BoNT/A. As shown in FIG. 2B, the sensor that contains SV2C fragment has an EC50 at 9.7 pM after four hours' incubation. This is approximately 5-fold more sensitive than the sensor without SV2C, indicating that including the fragment of toxin receptors may result in a more sensitive toxin sensor.

The third sensor protein was incubated with a gradient of BoNT/B. The remaining luciferase activities were measured and plotted as shown in FIG. 3A. The EC50, listed in FIG. 3B, is approximately 75.7 pM after 4 hours incubation. Incubating toxins with the sensor for 24 hours significantly improved the EC50 to 3.9 pM.

Advantage Compared to Available In Vitro Sensors:

These luciferase based toxin sensors provides similar sensitivity as fluorescence based sensors. The major advantage of these split luciferase based sensors is that they are not affected by the presence of serum albumin proteins.

Cell Based Assay:

An illustrative embodiment of a sensor for cell based assays is illustrated in FIG. 4. It contains a full length SNAP-25 between split NANOLUC™ luciferase fragments. In addition, it also contains a firefly luciferase between the N-nano and SNAP-25, which provides an internal control for expression levels of the sensor proteins in cells. This sensor protein is expressed in neurons via lentivirus mediated infection. Neurons were then exposed to various concentrations of BoNT/A. Cell lysates were harvested 48 hours later and the luciferase activities of both firefly luciferase and NANOLUC™ luciferase were measured. The levels of NANOLUC™ luciferase are normalized using firefly luciferase signals, and then normalized to the control neurons that were not exposed to any toxins (FIG. 4). Incubating neurons with toxins reduced the signals of NANOLUC™ luciferase (FIG. 4), with an EC50 at 2.9 pM.

Advantage Compared to Available Cell Based Assays:

The assay described herein provides sensitivity similar to the ELISA based assay established by Allergan. The major advantage of the present assay is that it does not require any special antibody. It is also easier, cheaper and faster than the ELISA assay.

It is specifically contemplated herein that toxin sensors and cell based assays as described herein offer faster, cheaper, and easier ways for pharmaceutical companies to measure and quantify the activity of BoNT/A and BoNT/B, potentially replacing the mouse bio-assay.

In Vitro and In Vivo Constructs for BoNTs Detection.

For BoNT/A detection, the construct was cloned into pET28a vector with NocI/NotI and the inserts were Nnano-SV2C(529-566)-G4S-SNAP25(141-206)-Cnano and Nnano-SNAP25(141-206)-Cnano ("G4S" disclosed as SEQ ID NO: 6). Split NANOLUC™ luciferase sequence is available from Promega. Overlap PCR was used to obtain full inserts and then inserts were ligated into a cut vector. For BoNT/B detection, the construct was Nnano-VAMP(35-96)-Cnano.

For BoNT/A in vivo detection, the constructs were designed either using split firefly or split NANOLUC, then the *renilla* and firefly as internal controls were separately applied. The internal control is located just in front of SNAP25 (Full length). The vector was based on pcDNA3.1 and syn-lox lentiviral vectors.

Cloning of In Vitro Assay Constructs

```
Sensor 1: NNano-SV2C-p25-CNano
NcoI-Nnano(1-159)-GSSGGGGSGGGGSSG-SacI-SV2C (529-566)-GGGGS-P25(141-206)-EcoRI-GSSGGGGSGGGSSG- Cnano(160-170)-NotI-His6-stop ("GSSGGGGSGGGGSSG" disclosed as SEQ ID NO: 4, "GGGGS" disclosed as SEQ ID NO: 6, "GSSGGGGSGGGSS G" disclosed as SEQ ID NO: 5 and "His6" disclosed as SEQ ID NO: 12)

Sensor 2: NNano-p25-CNano

NcoI-Nnano-(1-159)-GSSGGGGSGGGGSSG-SacIp25(141-206)-EcoRI-GSSGGGGSGGGSSG-Cnano(160-170)-

NotI-His6-stop ("GSSGGGGSGGGGSSG" disclosed as

SEQ ID NO: 4, "GSSGGGGSGGGSSG" disclosed as SEQ ID

NO: 5 and "His6" disclosed as SEQ ID NO: 12)

Sensor 3: NNano-hVAMP1-CNano

NcoI-Nnano-(1-159)-GSSGGGGSGGGGSSG-SacIhumanVAMP1(35-96)-EcoRI-GSSGGGGSGGGSSG-

Cnano(160-170)-NotI-His6-stop ("GSSGGGGSGGGGSSG"

disclosed as SEQ ID NO: 4, "GSSGGGGSGGGSSG"

disclosed as SEQ ID NO: 5 and "His6" disclosed as

SEQ ID NO: 12)

Cloning of in vivo assay construct

BamHI-Nnano-(1-159)-GSSGGGGSGGGGSSG-SacI-Firefly (Full length)-GGGGS-p25(FullLength)-EcoRI-GSSGGGGS GGGSSG-Cnano(160-170)-NotI (Stop codon) ("GGGGS"

disclosed as SEQ ID NO: 6 and "GSSGGGGSGGGSSG"

disclosed as SEQ ID NO: 5)
```

IMAC Purification of Sensor Proteins for In Vitro Assay.

Different constructs of sensor proteins were purified using Immobilized Metal Affinity Columns (IMAC). The His6 tag (SEQ ID NO: 12) was cloned into pET28a vector at C terminal. BL21 containing correct plasmid of in vitro construct was inoculated over night and cultivated at 37° C. until O.D. around 0.6-0.8, then induced by 0.25 mM of IPTG (final concentration) for over night at 20° C. The cells are harvested by centrifuging at 4500 g, 10 minutes. After that, cells pellets were dissolve in 50 mM HEPES, 150 mM NaCl, pH7.4 buffer and followed by sonication for 3 minutes. The supernatant of cell lysate was saved and mixed with Ni2+ beads for 1 h with rotation in 4° C. Later, the mixture was loaded into column and the resin was washed with 10 fold of bed column of 20 mM Imidizole in 50 mM HEPES, 150 mM NaCl, pH7.4 buffer. Finally, the protein was eluted in 4 fold of bed column 500 mM Imidizole in 50 mM HEPES, 150 mM NaCl, pH7.4 buffer. The purified sensor protein was dialyzed into 50 mM HEPES, pH 7.1 buffer to perform the assay immediately.

In Vitro Assay of Toxin Detection.

Sensor protein concentration is estimated by SDS-PAGE with standard BSA as reference. 30 nM of sensor protein was prepared in 50 mM HEPES, 20 μM ZnCl2, 2 mM DTT, 1 mg/ml BSA, pH 7.1 buffer. The botulinum toxin A was diluted and added into sensor protein solution with a concentration series from 1 nM to 1 fM with dilution factor 10. After 4 h and 24 h incubation at 37° C., Nano-Glo™ substrate (Promega) was added into each sample with equal volume. The luminescent signal was measured in plate reader. The assay was performed in duplicate. Negative controls were also designed and performed. BoNT/A was mixed with Nnano-VAMP-Cnano sensor protein or BoNT/B was mixed with Nnano-SV2C-p25-Cnano sensor protein.

In Vivo Assay (Cell Based Assay) of Toxin Detection.

Virus of dual luciferase construct (firefly as internal control and split NANOLUC™ for cleavage detection) was added into 7-days neuron cells and then botulinum toxin A of a series concentration from 300 pM to 1 pM was added into 13-day neuron cells with triplicate. After 48 h challenge with toxin, neuron cells were lysed by adding 200 μl passive lysis buffer (Promega) and incubated at room temperature for 20 minutes. 50 μl of cell lysate was mixed with 50 μl firefly luciferase substrate (ONE-Glo™ EX reagent) and light emissions measured. Subsequently, 50 μl NANO-LUC™ luciferase substrate (NanoDLR™ Stop & Glo (R) reagent) was added and light emissions measured.

| SEQ ID NO: | Description | Sequence |
|---|---|---|
| 23 | Human SNAP25<br>UniProtKB-P60880<br>(SNP25_HUMAN) | MAEDADMRNELEEMQRRADQLADESLESTRRMLQLVEESKDAG<br>IRTLVMLDEQGEQLERIEEGMDQINKDMKEAEKNLTDLGKFCG<br>LCVCPCNKLKSSDAYKKAWGNNQDGVVASQPARVVDEREQMAI<br>SGGFIRRVTNDARENEMDENLEQVSGIIGNLRHMALDMGNEID<br>TQNRQIDRIMEKADSNKTRIDEANQRATKMLGSG |
| 24 | Human VAMP-1<br>UniProtKB-P23763<br>(VAMP1_HUMAN): | MSAPAQPPAEGTEGTAPGGGPPGPPPNMTSNRRLQQTQAQVEE<br>VVDIIRVNVDKVLERDQKLSELDDRADALQAGASQFESSAAKL<br>KRKYWWKNCKMMIMLGAICAIIVVVIVIYFFT |
| 25 | Human VAMP-2<br>UniProtKB-P63027<br>(VAMP2_HUMAN) | MSATAATAPPAAPAGEGGPPAPPPNLTSNRRLQQTQAQVDEVV<br>DIMRVNVDKVLERDQKLSELDDRADALQAGASQFETSAAKLKR<br>KYWWKNLKMMIILGVICAIILIIIIVYFST |
| 26 | Human VAMP-3<br>UniProtKB-Q15836<br>(VAMP3_HUMAN): | MSTGPTAATGSNRRLQQTQNQVDEVVDIMRVNVDKVLERDQKL<br>SELDDRADALQAGASQFETSAAKLKRKYWWKNCKMWAIGITVL<br>VIFIIIIIVWVVSS |
| 27 | Human Syntaxin 1A<br>UniProtKB-Q16623<br>(STX1A_HUMAN) | MKDRTQELRTAKDSDDDDDVAVTVDRDRFMDEFFEQVEEIRGF<br>IDKIAENVEEVKRKHSAILASPNPDEKTKEELEELMSDIKKTA<br>NKVRSKLKSIEQSIEQEEGLNRSSADLRIRKTQHSTLSRKFVE<br>VMSEYNATQSDYRERCKGRIQRQLEITGRTTTSEELEDMLESG<br>NPAIFASGIIMDSSISKQALSEIETRHSEIIKLENSIRELHDM<br>FMDMAMLVESQGEMIDRIEYNVEHAVDYVERAVSDTKKAVKYQ<br>SKARRKKIMIIICCVILGIVIASTVGGIFA |
| 28 | Human Syntaxin 1B | mkdrtqelrs akdsddeeev vhvdrdhfmd effeqveeir<br>qcieklsedv eqvkkqhsai laapnpdekt kqeledltad<br>ikktankvrs klkaieqsie qeeglnrssa dlrirktqhs<br>tlsrkfvevm teynatqsky rdrckdriqr qleitgrttt<br>neeledmles gklaiftddi kmdsqmtkqa lneietrhne<br>iikletsire lhdmfvdmam lvesqgemid rieynvehsv<br>dyveravsdt kkavkyqska rrkkimiiic cvvlgvvlas<br>siggtlgl |

What is claimed herein is:

1. A method for determining potency of *C. botulinum* neurotoxin (BoNT), comprising:
   a) contacting the BoNT to a single chain polypeptide under conditions appropriate for BoNT activity, wherein the single chain polypeptide comprises:
      i) an N-terminal fragment of a reporter protein;
      ii) a linker comprising a BoNT cleavage site; and
      iii) a C-terminal fragment of the reporter protein; and
   b) determining reporter activity of the polypeptide, as compared to reporter activity of a reference, thereby determining potency,
   wherein the linker comprises a binding fragment of a receptor for the BoNT, and
   wherein the reference comprises no BoNT.

2. A method for detecting *C. botulinum* neurotoxin (BoNT) activity in a sample, comprising:
   a) contacting the sample to a single chain polypeptide under conditions appropriate for BoNT activity, wherein the single chain polypeptide comprises:
      i) an N-terminal fragment of a reporter protein;
      ii) a linker comprising a BoNT cleavage site; and
      iii) a C-terminal fragment of the reporter protein; and
   b) determining reporter activity of the polypeptide, as compared to reporter activity of the polypeptide in the absence of the sample, wherein a decrease of reporter activity indicates neurotoxin activity in the sample,
   wherein the linker comprises a binding fragment of a receptor for the BoNT.

3. The method of claim 2, wherein the step of contacting comprises contacting the BoNT to neuronal cells that express the single chain polypeptide and the method further comprises between the contacting step:
   incubating the neuronal cells for a period from about 12 hours to about 60 hours, and harvesting lysate from the neuronal cells.

* * * * *